(12) United States Patent
Luo et al.

(10) Patent No.: US 6,387,658 B1
(45) Date of Patent: May 14, 2002

(54) PCNA-ASSOCIATED CELL CYCLE PROTEINS, COMPOSITIONS AND METHODS OF USE

(75) Inventors: Ying Luo, Los Altos; Betty Huang, San Leandro, both of CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/404,627

(22) Filed: Sep. 23, 1999

(51) Int. Cl.[7] .......................... C07H 21/04; C07H 1/00; C07H 5/04; C07H 5/06; C07H 19/00

(52) U.S. Cl. ........................ 435/69.1; 536/1; 536/1.11; 536/18.7; 536/22.1; 536/23.1; 536/23.5; 530/350; 435/320.1

(58) Field of Search ........................ 536/1, 1.11, 18.7, 536/22.1, 23.1, 23.5; 530/350; 435/320.1, 69.1

(56) References Cited

FOREIGN PATENT DOCUMENTS

| WO | 98/41873 A | 9/1998 |
|---|---|---|
| WO | 99/31234 A | 6/1999 |
| WO | 99/54460 A | 10/1999 |

OTHER PUBLICATIONS

Amino acid and nucleic acid databases, Accession #AA682458, 1997.*
Ausubel et al. Short Protocols in Molecular Biology, second edition. pp. 16–4 to 16–9, 1992.*
National Cancer Institutute, Cancer Genome Anatomy Project (CGAP), Database EM_EST 'Online!, EMBL, Acc. No. AA954451 (XP–002162824) (1998).
Marra et al., Database EM_EST 'Online!, EMBL, Acc. No. AA879700 (XP–002162825) (1998).
National Cancer Institutute, Cancer Genome Anatomy Project (CGAP), Database EM_EST 'Online!, EMBL, Acc. No. AA63348 (XP–00216826) (1997).
Auffray et al., Database SWALL 'Online!, Acc. No. Q9NPP9 (XP–002162827) (2000).
Arroyo et al., "Mutant PCNA alleles are associated with cdc phenotypes and sensitivity to DNA damage in fission yeast," *Mol Gen Genet* 257:505–518 (1998).
Russel, P., "Checkpoints on the road to mitosis," *TIBS* 23(10)399–402 (1998).
Jonsson et al., "Proliferating cell nuclear antigen: more than a clamp for DNA polymerases," *BioEssays* 19(11):967–975 (1997).
Warbrick E., "PCNA binding through a conserved motif," *Bioessays*, 20(3):195–199 (1998).
Troelstra et al., "ERCC6, a member of a subfamily of putative helicases, is involved in Cockaynes's syndrome and preferential repair of active genes," *Cell*, 71(6):939–953 (1992).
Selby et al., "Human transcription–repair coupling factor CSB/ERCC6 is a DNA–stimulated ATPase but is not a helicase and does not disrupt the ternary transcription complex of stalled RNA polymerase II," *J. Biol. Chem.*, 272(3):1885–1890 (1997).
Huang et al., "A possible yeast homolog of human active–gene–repairing helicase ERCC6+," *Biochem. Biophys. Res. Commun.*, 201(1):310–317 (1994).
van Gool et al., "RAD26, the functional S. cerevisiae homolog of the Cockayne syndrome B gene ERCC6," *EMBO J.*, 13(22):5361–5369 (1994).
Tijsterman et al., "Rad26, the yeast homolog of the cockayne syndrome B gene product, conteracts inhibition of DNA repair due to RNA polymerase II transcription," *J. Biol. Chem.*, 274(3):1199–1202 (1999).
Shimizu et al., "Purification and characterization of DNA helicase III from the yeast *Saccharomyces cerevisiae*," *J. Biol. Chem.*, 268(13):9578–9584 (1993).
Aboussekhra et al., "RADH, a gene of *Saccharomyces cerevisiae* encoding a putative DNA helicase involved in DNA repair. Characteristics of radH mutants and sequence of the gene," *Nucleic Acids*, 17(18):7211–7219(1989).
Kelman et al., "Protein–PCNA interactions: a DNA–scanning mechanism?" *Trends Biochem. Sci.*, 23(7):236–238 (1998).
Fotedar et al., "Cell cycle control of DNA replication," *Prog. Cell Cycle Res.*, 1:73–89 (1995).
Prosperi, E., "Multiple roles of the proliferating cell nuclear antigen: DNA replication, repair and cell cycle control," *Prog. Cell Cycle Res.*, 3:193–210 (1997).
Kolodner et al., "Eukaryotic DNA mismatch repair," *Curr. Opin. Genetic Dev.*, 9(1):89–96 (1999).

* cited by examiner

*Primary Examiner*—Anthony C. Caputa
*Assistant Examiner*—Alana M. Harris
(74) *Attorney, Agent, or Firm*—Flehr Hohbach Test Albritton & Herbert LLP; Robin M. Silva, Esq.

(57) ABSTRACT

The present invention is directed to novel polypeptides, nucleic acids and related molecules which have an effect on or are related to the cell cycle. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided by the present invention are methods for identifying novel compositions which mediate cell cycle bioactivity, and the use of such compositions in diagnosis and treatment of disease.

13 Claims, 5 Drawing Sheets

```
GCGGGGGTTAGGAGACGGAAGTCAGAGCCTAGGAAGATTTGGGGGTCGCCTTGCCGGCCT
CCTGTCCTCCTCCGGCGGCGGCGGAGCCCGAGAGGACTAGGTGAACACCGCTTTGCCAGC
CTCACACAGCGTCCCCTGGCTCTGCCGCCGCTCCGGACGTCGCCCTCCCGTTCTGCTTGG
GTCCCCTTAGTCGCTACCTTTGCTGGGATCCCCCTCCTCCATCCTGTGGCTTCGGGTTGC
CGAAGAGCGATGCTCGGAGGGCGGCCGGAAGTGGCGTTGGCCGCCATTGGCCTGCCGGCC
AGCCACCTTGCTGTCCTCCGCCGCCTTCCGGGTGTTACATGCAGCCGGGCTCGGCCCCTC
CCCCTGGCCGGATGGATCCGTCGGCGCCACAGCCCCGCGCGGAAACCTCAGGCAAAGACA
TATGGCATCCAGGAGAAAGATGTCTTGCCCCTTCTCCAGATAATGGAAAACTTTGTGAAG
CAAGCATAAAATCTATCACAGTGGATGAAAATGGCAAGTCATTTGCAGTCGTCTTATATG
CAGATTTTCAAGAAAGGAAAATACCTCTTAAACAGCTTCAAGAAGTGAAATTTGTTAAAG
ATTGCCCTAGGAATCTTATATTTGATGATGAAGATTTAGAAAAACCTTATTTCCCAAACC
GAAAATTTCCATCATCTTCTGTTGCTTTTAAATTATCTGACAATGGAGACTCTACTCCTT
ATACCATCAATAGGTATTTGAGAGACTACCAAAGAGAAGGAACCCGGTTTCTTTATGGAC
ACTACATCCATGGAGGAGGTGCATTCTGGGTGATGACATGGGACTTGGAAAAACAGTAC
AGGTTATTTCATTTCTGGCTGCAGTTTTGCATAAAAAGGGAACTCGTGAGGATATTGAAA
ATAACATGCCAGAGTTTTTACTAAGAAGTATGAAAAGGAACCCCTTTCTTCTACAGCAA
AAAAGATGTTCTTAATAGTTGCTCCTCTTTCTGTCCTCTACAACTGGAAGGATGAATTGG
ACACCTGGGGATATTTCAGAGTCACTGTTTTACATGGAAACAGAAAAGATAATGAATTAA
TTCGTGTAAAGCAGAGGAAATGTGAAATTGCTCTAACAACTTATGAAACACTACGCTTAT
GCCTGGATGAACTTAACAGTTTGGAATGGTCAGCTGTCATTGTGGATGAAGCTCATAGAA
TCAAGAATCCAAAAGCTAGAGTAACAGAAGTTATGAAAGCTTTGAAATGTAATGTCCGCA
TTGGCCTCACTGGAACCATCCTTCAGAACAACATGAAGGAACTGTGGTGTGTTATGGACT
GGGCTGTGCCAGGCCTTTTAGGGAGTGGGACCTACTTCAAGAAGCAGTTTTCTGACCCAG
TAGAACATGGTCAGAGACACACGGCAACAAAGAGAGAACTAGCCACTGGCCGAAAGGCCA
TGCAAAGACTTGCCAAAAAGATGTCTGGCTGGTTTCTCAGGCGCACCAAGACTCTTATCA
AGGATCAGTTGCCTAAGAAGGAAGACCGGATGGTGTATTGTTCTTTGACAGATTTCCAGA
AAGCTGTCTATCGAACAGTGTTAGAAACAGAGGACGTGACTTTGATACTTCAATCTTCTG
AGCCTTGTACCTGTAGGAGTGGCCAAAAAAGGAGAAATTGTTGTTATAAGACCAATTCTC
ATGGTGAAACAGTGAAAACCTTGTATCTCAGTTACCTTACAGTCCTTCAGAAGGTAGCTA
ACCATGTCGCGCTACTGCAAGCTGCTAGTACTTCCAAACAACAGGAAACACTTATCAAAA
GGATATGTGATCAGGTATTTTCCAGATTCCCAGATTTTGTGCAGAAAAGCAAAGATGCAG
CCTTTGAAACACTTTCTGACCCTAAATACAGTGGAAAATGAAGGTCCTTCAGCAGCTTT
TAAATCATTGCAGGAAAAACAGAGATAAAGTTCTTCTCTTTTCTTTTTCCACCAAGTTGC
TTGACGTGCTACAGCAGTACTGTATGGCGTCTGGGCTTGATTACCGACGACTTGATGGAA
GTACAAAATCAGAGGAAAGACTCAAGATTGTAAAAGAGTTCAACAGTACACAAGATGTTA
ACATTTGCCTTGTCTCTACAATGGCTGGTGGACTAGGCCTCAATTTTGTCGGTGCCAATG
TTGTTGTATTATTTGATCCTACTTGGAATCCAGCCAATGATCTTCAAGCCATTGACAGAG
CATATAGGATTGGACAATGTAGAGATGTCAAAGTGCTTAGGCTGATATCCTTGGGAACTG
TGGAGGAAATCATGTATTTACGACAGATATACAAGCAGCAACTTCACTGTGTGGTGGTTG
GAAGTGAAAATGCCAAACGATATTTTGAAGCAGTTCAAGGATCTAAAGAGCATCAAGGAG
AGCTTTTTGGGATCCATAACCTCTTCAAATTTAGGTCCCAAGGGTCTTGTCTTACGAAGG
ACATCCTGGAGAGAGAAGGCCAAGTAGAAGCAGGGATCATGACAGCCACAACATGGTTGA
AAGAGGGACCTCCAGCACACAAACTGGAAATGCCTAGACAGCCTGACTGTCAGGAATGCA
```

FIG._1A

```
GAGGTACAGAACAAGCTGCAGAGCCACTGGCAAAGGAAGCATGTGATCTCTGCAGTGACT
TCAGTGATGAAGAGCCAGTGGGAGCCACAGGAATAAAGACTGCCAAAAACAAAGCACCCG
ATTCAAGTAAAGCTTCCAGCTCTCCAGGACAGCTTACCTTACTCCAGTGTGGTTTCTCGA
AATTGCTTGAAACAAAATGTAAAGCAGTTGAGGATAGTGATGGAAATACTGCCTCTGATG
ATGAAAGTTCTGATGAGCAGCCCACATGCCTTTCAACAGAAGCCAAAGATGCTGGTTGTG
AGAAAAATCAGGACTCTCTTGGTACTTCAAAACATCAGAAATTAGATAACATCCTAAATC
CAAAAGAAAGCATATTTTTTATAAAAGTGAGAAGATTTTAGAACAGAATATTTCTTCCA
AGTCTGACGAGAAAAAAATTAAAAATACAGATAAACATTGCATTTTACAGAATGTCACAG
AATCAGAAGATAGTGATGTCATCTGTCCTACACAATACACAACTGAGAGATTCCCCGACA
ATAGTCTAAGGTTTAAGCCACCCTTGGAAGGATCTGAGGATTCTGAAACAGAACACACTG
TAAAAACAAGAAATAATGATAATAGTCGAAACACTGATGACAAAAGAAATGGAATAATTT
CAAAAAAGTTAAGTCCTGAGAACACAACCCTGAAATCTATTTTGAAAAGAAAAGGCACCA
GTGATATCAGTGATGAATCTGATGACATTGAAATTTCTTCCAAGTCAAGAGTAAGAAAGA
GAGCTAGTTCATTGAGGTTTAAGAGAATAAAAGAAACCAAAAAAGAACTTCACAATTCTC
CCAAAACAATGAACAAAACAAACCAAGTGTATGCAGCAAATGAGGATCATAACTCTCAGT
TTATTGATGATTATTCATCCTCAGATGAGAGTTTATCCGTCAGCCACTTCAGTTTCTCTA
AACAGAGCCACAGACCAAGAACTATAAGAGACAGAACTAGTTTTTCTTCAAAATTGCCTA
GCCATAATAAGAAAAATAGCACTTTTATTCCAAGAAAACCAATGAAATGTTCAAATGAGA
AAGTTGTTAATCAAGAGCAGTCGTATGAATCAATGGATAAATTTTTAGATGGCGTTCAGG
AAGTGGCTTATATTCACTCAAACCAGAATGTAATTGGATCGAGCAAAGCTGAAAATCACA
TGAGCCGATGGGCAGCACATGACGTATTTGAGTTGAAGCAGTTTTCTCAGCTGCCTGCTA
ACATAGCTGTTTGCAGTTCTAAGACATATAAAGAAAAGTGGATGCAGATACATTGCCAC
ACACAAAGAAAGGCCAGCAACCGAGTGAAGGCAGCATTTCACTTCCTCTTTACATTTCAA
ATCCTGTAAACCAGAAGAAGAAAAAGTCTACCATACAAACCAGACCACCTTCATAATTG
GAGAAACACCAAAGGAATCCGCAGGTATATTGTCTCTGACAATACTATACTTGAAGAAT
AATTCTCAAAGGAAATGTAGCTCATTAGTAAAATATGTAAATACTTGAATTATAACCATA
ACTGACATCTGAATATTTCAGAAAAATCTGAATTTCAAAAATAAACTGCAAATGTTTTAG
ATGCT
```

FIG._1B

```
   1   MQPGSAPPPGRMDPSAPQPRAETSGKDIWHPGERCLAPSPDNGKLCEASIKSITVDENGK
  61   SFAVVLYADFQERKIPLKQLQEVKFVKDCPRNLIFDDEDLEKPYFPNRKFPSSSVAFKLS
 121   DNGDSTPYTINRYLRDYQREGTRFLYGHYIHGGGCILGDDMGLGKTVQVISFLAAVLHKK
 181   GTREDIENNMPEFLLRSMKKEPLSSTAKKMFLIVAPLSVLYNWKDELDTWGYFRVTVLHG
 241   NRKDNELIRVKQRKCEIALTTYETLRLCLDELNSLEWSAVIVDEAHRIKNPKARVTEVMK
 301   ALKCNVRIGLTGTILQNNMKELWCVMDWAVPGLLGSGTYFKKQFSDPVEHGQRHTATKRE
 361   LATGRKAMQRLAKKMSGWFLRRTKTLIKDQLPKKEDRMVYCSLTDFQKAVYRTVLETEDV
 421   TLILQSSEPCTCRSGQKRRNCCYKTNSHGETVKTLYLSYLTVLQKVANHVALLQAASTSK
 481   QQETLIKRICDQVFSRFPDFVQKSKDAAFETLSDPKYSGKMKVLQQLLNHCRKNRDKVLL
 541   FSFSTKLLDVLQQYCMASGLDYRRLDGSTKSEERLKIVKEFNSTQDVNICLVSTMAGGLG
 601   LNFVGANVVVLFDPTWNPANDLQAIDRAYRIGQCRDVKVLRLISLGTVEEIMYLRQIYKQ
 661   QLHCVVVGSENAKRYFEAVQGSKEHQGELFGIHNLFKFRSQGSCLTKDILEREGQVEAGI
 721   MTATTWLKEGPPAHKLEMPRQPDCQECRGTEQAAEPLAKEACDLCSDFSDEEPVGATGIK
 781   TAKNKAPDSSKASSSPGQLTLLQCGFSKLLETKCKAVEDSDGNTASDDESSDEQPTCLST
 841   EAKDAGCEKNQDSLGTSKHQKLDNILNPKEKHIFYKSEKILEQNISSKSDEKKIKNTDKH
 901   CILQNVTESEDSDVICPTQYTTERFPDNSLRFKPPLEGSEDSETEHTVKTRNNDNSRNTD
 961   DKRNGIISKKLSPENTTLKSILKRKGTSDISDESDDIEISSKSRVRKRASSLRFKRIKET
1021   KKELHNSPKTMNKTNQVYAANEDHNSQFIDDYSSSDESLSVSHFSFSKQSHRPRTIRDRT
1081   SFSSKLPSHNKKNSTFIPRKPMKCSNEKVVNQEQSYESMDKFLDGVQEVAYIHSNQNVIG
1141   SSKAENHMSRWAAHDVFELKQFSQLPANIAVCSSKTYKEKVDADTLPHTKKGQQPSEGSI
1201   SLPLYISNPVNQKKKKVYHTNQTTFIIGETPKGIRRYIVSDNTILEE
```

FIG._2

```
CATATGGCATCCAGGAGAAAGATGTCTTGCCCCTTCTCCAGATAATGGAAAACTTTGTGA
AGCAAGCATAAAATCTATCACAGTGGATGAAAATGGCAAGTCATTTGCAGTCGTCTTATA
TGCAGATTTTCAAGAAAGGAAAATACCTCTTAAACAGCTTCAAGAAGTGAAATTTGTTAA
AGATTGCCCTAGGAATCTTATATTTGATGATGAAGATTTAGAAAAACCTTATTTCCCAAA
CCGAAAATTTCCATCATCTTCTGTTGCTTTTAAATTATCTGACAATGGAGACTCTACTCC
TTATACCATCAATAGGTATTTGAGAGACTACCAAAGAGAAGGAACCCGGTTTCTTTATGG
ACACTACATCCATGGAGGAGGGTGCATTCTGGGTGATGACATGGGACTTGGAAAAACAGT
ACAGGTTATTTCATTTCTGGCTGCAGTTTTGCATAAAAAGGGAACTCGTGAGGATATTGA
AAATAACATGCCAGAGTTTTTACTAAGAAGTATGAAAAAGGAACCCCTTTCTTCTACAGC
AAAAAAGTTTGGAATGGTCAGCTGTCATTGTGGATGAAGCTCATAGAATCAAGAATCCAA
AAGCTAGAGTAACAGAAGTTATGAAAGCTTTGAAATGTAATGTCCGCATTGGCCTCACTG
GAACCATCCTTCAGAACAACATGAAGGAACTGTGGTGTGTTATGGACTGGGCTGTGCCAG
GCCTTTTAGGGAGTGGGACCTACTTCAAGAAGCAGTTTTCTGACCCAGTAGAACATGGTC
AGAGACACACGGCAACAAAGAGAGAACTAGCCACTGGCCGAAAGGCCATGCAAAGACTTG
CCAAAAAGATGTCTGGCTGGTTTCTCAGGCGCACCAAGACTCTTATCAAGGATCAGTTGC
CTAAGAAGGAAGACCGGATGGTGTATTGTTCTTTGACAGATTTCCAGAAAGCTGTCTATC
GAACAGTGTTAGAAACAGAGGACGTGACTTTGATACTTCAATCTTCTGAGCCTTGTACCT
GTAGGAGTGGCCAAAAAAGGAGAAATTGTTGTTATAAGACCAATTCTCATGGTGAAACAG
TGAAAACCTTGTATCTCAGTTACCTTACAGTCCTTCAGAAGGTAGCTAACCATGTCGCGC
TACTGCAAGCTGCTAGTACTTCCAAACAACAGGAAACACTTATCAAAAGGATATGTGATC
AGGTATTTTCCAGATTCCCAGATTTTGTGCAGAAAAGCAAAGATGCAGCCTTTGAAACAC
TTTCTGACCCTAAATACAGTGGAAAATGAAGGTCCTTCAGCAGCTTTTAAATCATTGCA
GGAAAAACAGAGATAAAGTTCTTCTCTTTTCTTTTTCCACCAAGTTGCTTGACGTGCTAC
AGCAGTACTGTATGGCGTCTGGGCTTGATTACCGACGACTTGATGGAAGTACAAAATCAG
AGGAAAGACTCAAGATTGTAAAAGAGTTCAACAGTACACAAGATGTTAACATTTGCCTTG
TCTCTACAATGGCTGGTGGACTAGGCCTCAATTTTGTCGGTGCCAATGTTGTTGTATTAT
TTGATCCTACTTGGAATCCAGCCAATGATCTTCAAGCCATTGACAGAGCATATAGGATTG
GACAATGTAGAGATGTCAAAGTGCTTAGGCTGATATCCTTGGGAACTGTGGAGGAAATCA
TGTATTTACGACAGATATACAAGCAGCAACTTCACTGTGTGGTGGTTGGAAGTGAAAATG
CCAAACGATATTTTGAAGCAGTTCAAGGATCTAAAGAGCATCAAGGAGAGCTTTTGGGA
TCCATAACCTCTTCAAATTTAGGTCCCAAGGGTCTTGTCTTACGAAGGACATCCTGGAGA
GAGAAGGCCAAGTAGAAGCAGGGATCATGACAGCCACAACATGGTTGAAAGAGGGACCTC
CAGCACACAAACTGGAAATGCCTAGACAGCCTGACTGTCAGGAATGCAGAGGTACAGAAC
AAGCTGCAGAGCCACTGGCAAAGGAAGCATGTGATCTCTGCAGTGACTTCAGTGATGAAG
AGCCAGTGGGAGCCACAGGAATAAAGACTGCCAAAAACAAAGCACCCGATTCAAGTAAAG
CTTCCAGCTCTCCAGGACAGCTTACCTTACTCCAGTGTGGTTTCTCGAAATTGCTTGAAA
CAAAATGTAAAGCAGTTGAGGATAGTGATGGAAATACTGCCTCTGATGATGAAGTTCTG
ATGAGCAGCCCACATGCCTTTCAACAGAAGCCAAAGATGCTGGTTGTGAGAAAAATCAGG
ACTCTCTTGGTACTTCAAAACATCAGAAATTAGATAACATCCTAAATCCAAAAGAAAAGC
ATATTTTTTATAAAAGTGAGAAGATTTTAGAACAGAATATTTCTTCCAAGTCTGACGAGA
AAAAAATTAAAAATACAGATAAACATTGCATTTTACAGAATGTCACAGAATCAGAAGATA
GTGATGTCATCTGTCCTACACAATACACAACTGAGAGATTCCCCGACAATAGTCTAAGGT
TTAAGCCACCCTTGGAAGGATCTGAGGATTCTGAAACAGAACACACTGTAAAAACAAGAA
```

*FIG._3A*

```
ATAATGATAATAGTCGAAACACTGATGACAAAAGAAATGGAATAATTTCAAAAAAGTTAA
GTCCTGAGAACACAACCCTGAAATCTATTTTGAAAAGAAAAGGCACCAGTGATATCAGTG
ATGAATCTGATGACATTGAAATTTCTTCCAAGTCAAGAGTAAGAAAGAGAGCTAGTTCAT
TGAGGTTTAAGAGAATAAAAGAAACCAAAAAAGAACTTCACAATTCTCCCAAAACAATGA
ACAAAACAAACCAAGTGTATGCAGCAAATGAGGATCATAACTCTCAGTTTATTGATGATT
ATTCATCCTCAGATGAGAGTTTATCCGTCAGCCACTTCAGTTTCTCTAAACAGAGCCACA
GACCAAGAACTATAAGAGACAGAACTAGTTTTTCTTCAAAATTGCCTAGCCATAATAAGA
AAAATAGCACTTTTATTCCAAGAAAACCAATGAAATGTTCAAATGAGAAAGTTGTTAATC
AAGAGCAGTCGTATGAATCAATGGATAAATTTTAGATGGCGTTCAGGAAGTGGCTTATA
TTCACTCAAACCAGAATGTAATTGGATCGAGCAAAGCTGAAAATCACATGAGCCGATGGG
CAGCACATGACGTATTTGAGTTGAAGCAGTTTTCTCAGCTGCCTGCTAACATAGCTGTTT
GCAGTTCTAAGACATATAAAGAAAAGTGGATGCAGATACATTGCCACACACAAAGAAAG
GCCAGCAACCGAGTGAAGGCAGCATTTCACTTCCTCTTTACATTTCAAATCCTGTAAACC
AGAAGAAGAAAAAGTCTACCATACAAACCAGACCACCTTCATAATTGGAGAAACACCAA
AAGGAATCCGCAGGTATATTGTCTCTGACAATACTATACTTGAAGAATAATTCTCAAAGG
AAATGTAGCTCATTAGTAAAATATGTAAATACTTGAATTATAACCATAACTGACATCTGA
ATATTTCAGAAAAATCTGAATTTCAAAAATAAACTGCAAATGTTTTAGATGCT
```

*FIG._3B*

```
MKALKCNVRIGLTGTILQNNMKELWCVMDWAVPGLLGSGTYFKKQFSDPVEHGQRHTATK
RELATGRKAMQRLAKKMSGWFLRRTKTLIKDQLPKKEDRMVYCSLTDFQKAVYRTVLETE
DVTLILQSSEPCTCRSGQKRRNCCYKTNSHGETVKTLYLSYLTVLQKVANHVALLQAAST
SKQQETLIKRICDQVFSRFPDFVQKSKDAAFETLSDPKYSGKMKVLQQLLNHCRKNRDKV
LLFSFSTKLLDVLQQYCMASGLDYRRLDGSTKSEERLKIVKEFNSTQDVNICLVSTMAGG
LGLNFVGANVVVLFDPTWNPANDLQAIDRAYRIGQCRDVKVLRLISLGTVEEIMYLRQIY
KQQLHCVVVGSENAKRYFEAVQGSKEHGELFGIHNLFKFRSQGSCLTKDILEREGQVEA
GIMTATTWLKEGPPAHKLEMPRQPDCQECRGTEQAAEPLAKEACDLCSDFSDEEPVGATG
IKTAKNKAPDSSKASSSPGQLTLLQCGFSKLLETKCKAVEDSDGNTASDDESSDEQPTCL
STEAKDAGCEKNQDSLGTSKHQKLDNILNPKEKHIFYKSEKILEQNISSKSDEKKIKNTD
KHCILQNVTESEDSDVICPTQYTTERFPDNSLRFKPPLEGSEDSETEHTVKTRNNDNSRN
TDDKRNGIISKKLSPENTTLKSILKRKGTSDISDESDDIEISSKSRVRKRASSLRFKRIK
ETKKELHNSPKTMNKTNQVYAANEDHNSQFIDDYSSSDESLSVSHFSFSKQSHRPRTIRD
RTSFSSKLPSHNKKNSTFIPRKPMKCSNEKVVNQEQSYESMDKFLDGVQEVAYIHSNQNV
IGSSKAENHMSRWAAHDVFELKQFSQLPANIAVCSSKTYKEKVDADTLPHTKKGQQPSEG
SISLPLYISNPVNQKKKKVYHTNQTTFIIGETPKGIRRYIVSDNTILEE
```

*FIG._4*

SEQUENCE LISTING

```
<160> NUMBER OF SEQ ID NOS:  11

<210> SEQ ID NO 1
<211> LENGTH: 4205
<212> TYPE: DNA
<213> ORGANISM: Homo sapiens

<400> SEQUENCE: 1
gcgggggtta ggagacggaa gtcagagcct aggaagattt gggggtcgcc ttgccggcct      60
cctgtcctcc tccggcggcg gcggagcccg agaggactag gtgaacaccg ctttgccagc     120
ctcacacagc gtccctggc tctgccgccg ctccggacgt cgccctcccg ttctgcttgg     180 gtcccttag tcgctacctt tgctgggatc ccctcctcc atcctgtggc ttcgggttgc      240
cgaagagcga tgctcggagg gcggccggaa gtggcgttgg ccgccattgg cctgccggcc     300
agccaccttg ctgtcctccg ccgccttccg ggtgttacat gcagccgggc tcggcccctc     360
```

-continued

```
cccctggccg gatggatccg tcggcgccac agcccgcgc ggaaacctca ggcaaagaca      420
tatggcatcc aggagaaaga tgtcttgccc cttctccaga taatggaaaa ctttgtgaag      480
caagcataaa atctatcaca gtggatgaaa atggcaagtc atttgcagtc gtcttatatg      540
cagattttca agaaaggaaa atacctctta aacagcttca agaagtgaaa tttgttaaag      600
attgccctag gaatcttata tttgatgatg aagatttaga aaaaccttat ttcccaaacc      660
gaaaatttcc atcatcttct gttgctttta aattatctga caatggagac tctactcctt      720
ataccatcaa taggtatttg agagactacc aaagagaagg aacccggttt ctttatggac      780
actacatcca tggaggaggg tgcattctgg gtgatgacat gggacttgga aaaacagtac      840
aggttatttc atttctggct gcagttttgc ataaaaaggg aactcgtgag gatattgaaa      900
ataacatgcc agagttttta ctaagaagta tgaaaaagga ccccttttct tctacagcaa      960
aaaagatgtt cttaatagtt gctcctcttt ctgtcctcta caactggaag gatgaattgg     1020
acacctgggg atatttcaga gtcactgttt tacatggaaa cagaaaagat aatgaattaa     1080
ttcgtgtaaa gcagaggaaa tgtgaaattg ctctaacaac ttatgaaaca ctacgcttat     1140
gcctggatga acttaacagt ttggaatggt cagctgtcat tgtggatgaa gctcatagaa     1200
tcaagaatcc aaaagctaga gtaacagaag ttatgaaagc tttgaaatgt aatgtccgca     1260
ttggcctcac tggaaccatc cttcagaaca acatgaagga actgtggtgt gttatggact     1320
gggctgtgcc aggcctttta gggagtggga cctacttcaa gaagcagttt tctgacccag     1380
tagaacatgg tcagagacac acggcaacaa agagagaact agccactggc cgaaaggcca     1440
tgcaaagact tgccaaaaag atgtctggct ggtttctcag gcgcaccaag actcttatca     1500
aggatcagtt gcctaagaag gaagaccgga tggtgtattg ttctttgaca gatttccaga     1560
aagctgtcta tcgaacagtg ttagaaacag aggacgtgac tttgatactt caatcttctg     1620
agccttgtac ctgtaggagt ggccaaaaaa ggagaaattt tgttataag accaattctc     1680 atggtgaaac agtgaaaacc ttgtatctca gttaccttac agtccttcag aaggtagcta     1740
accatgtcgc gctactgcaa gctgctagta cttccaaaca acaggaaaca cttatcaaaa     1800
ggatatgtga tcaggtattt tccagattcc cagattttgt gcagaaaagc aaagatgcag     1860
cctttgaaac actttctgac cctaaataca gtggaaaaat gaaggtcctt cagcagcttt     1920
taaatcattg caggaaaaac agagataaag ttcttctctt ttcttttttcc accaagttgc     1980 ttgacgtgct acagcagtac tgtatggcgt ctgggcttga ttaccgacga cttgatggaa     2040
gtacaaaatc agaggaaaga ctcaagattg taaaagagtt caacagtaca caagatgtta     2100
acatttgcct tgtctctaca atggctggtg gactaggcct caattttgtc ggtgccaatg     2160
ttgttgtatt atttgatcct acttggaatc cagccaatga tcttcaagcc attgacagag     2220
catataggat tggacaatgt agagatgtca agtgcttag gctgatatcc ttgggaactg     2280
tggaggaaat catgtatttt cgacagatat acaagcagca acttcactgt gtggtggttg     2340
gaagtgaaaa tgccaaacga tattttgaag cagttcaagg atctaaagag catcaaggag     2400 agcttttttgg gatccataac ctcttcaaat ttaggtccca agggtcttgt cttacgaagg     2460
acatcctgga gagagaaggc caagtagaag caggggatcat gacagccaca acatggttga     2520 agagggacc tccagcacac aaactggaaa tgcctagaca gcctgactgt caggaatgca     2580
gaggtacaga acaagctgca gagccactgg caaaggaagc atgtgatctc tgcagtgact     2640
tcagtgatga agagccagtg ggagccacag gaataaagac tgccaaaaac aaagcacccg     2700
attcaagtaa agcttccagc tctccaggac agcttacctt actccagtgt ggtttctcga     2760
```

```
aattgcttga acaaaatgt aaagcagttg aggatagtga tggaaatact gcctctgatg   2820
atgaaagttc tgatgagcag cccacatgcc tttcaacaga agccaaagat gctggttgtg   2880
agaaaaatca ggactctctt ggtacttcaa acatcagaa attagataac atcctaaatc    2940
caaaagaaaa gcatattttt tataaaagtg agaagatttt agaacagaat atttcttcca   3000
agtctgacga gaaaaaatt aaaatacag ataaacattg cattttacag aatgtcacag     3060
aatcagaaga tagtgatgtc atctgtccta cacaatacac aactgagaga ttccccgaca   3120
atagtctaag gtttaagcca cccttggaag gatctgagga ttctgaaaca gaacacactg   3180
taaaaacaag aaataatgat aatagtcgaa acactgatga caaagaaat ggataatttt    3240 caaaaaagtt aagtcctgag aacacaaccc tgaaatctat tttgaaaaga aaggcacca    3300 gtgatatcag tgatgaatct gatgacattg aaatttcttc caagtcaaga gtaagaaaga   3360
gagctagttc attgaggttt aagagaataa agaaaccaa aaaagaactt cacaattctc    3420
ccaaaacaat gaacaaaaca aaccaagtgt atgcagcaaa tgaggatcat aactctcagt   3480
ttattgatga ttattcatcc tcagatgaga gtttatccgt cagccacttc agtttctcta   3540
aacagagcca cagaccaaga actataagag acagaactag ttttttcttca aaattgccta   3600 gccataataa gaaaaatagc acttttattc caagaaaacc aatgaaatgt caaatgaga    3660 aagttgttaa tcaagagcag tcgtatgaat caatggataa atttttagat ggcgttcagg   3720
aagtggctta tattcactca aaccagaatg taattggatc gagcaaagct gaaaatcaca   3780
tgagccgatg ggcagcacat gacgtatttg agttgaagca gttttctcag ctgcctgcta   3840
acatagctgt ttgcagttct aagacatata agaaaaagt ggatgcagat acattgccac    3900
acacaaagaa aggccagcaa ccgagtgaag gcagcatttc acttcctctt tacatttcaa   3960
atcctgtaaa ccagaagaag aaaaaagtct accatacaaa ccagaccacc ttcataattg   4020
gagaaacacc aaaaggaatc cgcaggtata ttgtctctga caatactata cttgaagaat   4080
aattctcaaa ggaaatgtag ctcattagta aaatatgtaa atacttgaat tataaccata   4140
actgacatct gaatatttca gaaaaatctg aatttcaaaa ataaactgca aatgttttag   4200
atgct                                                               4205
```

<210> SEQ ID NO 2
<211> LENGTH: 1247
<212> TYPE: PRT
<213> ORGANISM: Homo sapiens

<400> SEQUENCE: 2

```
Met Gln Pro Gly Ser Ala Pro Pro Gly Arg Met Asp Pro Ser Ala
 1               5                  10                  15

Pro Gln Pro Arg Ala Glu Thr Ser Gly Lys Asp Ile Trp His Pro Gly
                20                  25                  30

Glu Arg Cys Leu Ala Pro Ser Pro Asp Asn Gly Lys Leu Cys Glu Ala
            35                  40                  45

Ser Ile Lys Ser Ile Thr Val Asp Glu Asn Gly Lys Ser Phe Ala Val
        50                  55                  60

Val Leu Tyr Ala Asp Phe Gln Glu Arg Lys Ile Pro Leu Lys Gln Leu
    65                  70                  75                  80

Gln Glu Val Lys Phe Val Lys Asp Cys Pro Arg Asn Leu Ile Phe Asp
                85                  90                  95

Asp Glu Asp Leu Glu Lys Pro Tyr Phe Pro Asn Arg Lys Phe Pro Ser
            100                 105                 110
```

-continued

```
Ser Ser Val Ala Phe Lys Leu Ser Asp Asn Gly Asp Ser Thr Pro Tyr
        115                 120                 125
Thr Ile Asn Arg Tyr Leu Arg Asp Tyr Gln Arg Glu Gly Thr Arg Phe
        130                 135                 140
Leu Tyr Gly His Tyr Ile His Gly Gly Cys Ile Leu Gly Asp Asp
145                 150                 155                 160
Met Gly Leu Gly Lys Thr Val Gln Val Ile Ser Phe Leu Ala Ala Val
                165                 170                 175
Leu His Lys Lys Gly Thr Arg Glu Asp Ile Glu Asn Asn Met Pro Glu
                180                 185                 190
Phe Leu Leu Arg Ser Met Lys Lys Glu Pro Leu Ser Ser Thr Ala Lys
                195                 200                 205
Lys Met Phe Leu Ile Val Ala Pro Leu Ser Val Leu Tyr Asn Trp Lys
        210                 215                 220
Asp Glu Leu Asp Thr Trp Gly Tyr Phe Arg Val Thr Val Leu His Gly
225                 230                 235                 240
Asn Arg Lys Asp Asn Glu Leu Ile Arg Val Lys Gln Arg Lys Cys Glu
                245                 250                 255
Ile Ala Leu Thr Thr Tyr Glu Thr Leu Arg Leu Cys Leu Asp Glu Leu
                260                 265                 270
Asn Ser Leu Glu Trp Ser Ala Val Ile Val Asp Glu Ala His Arg Ile
        275                 280                 285
Lys Asn Pro Lys Ala Arg Val Thr Glu Val Met Lys Ala Leu Lys Cys
        290                 295                 300
Asn Val Arg Ile Gly Leu Thr Gly Thr Ile Leu Gln Asn Asn Met Lys
305                 310                 315                 320
Glu Leu Trp Cys Val Met Asp Trp Ala Val Pro Gly Leu Leu Gly Ser
                325                 330                 335
Gly Thr Tyr Phe Lys Lys Gln Phe Ser Asp Pro Val Glu His Gly Gln
                340                 345                 350
Arg His Thr Ala Thr Lys Arg Glu Leu Ala Thr Gly Arg Lys Ala Met
        355                 360                 365
Gln Arg Leu Ala Lys Lys Met Ser Gly Trp Phe Leu Arg Arg Thr Lys
        370                 375                 380
Thr Leu Ile Lys Asp Gln Leu Pro Lys Lys Glu Asp Arg Met Val Tyr
385                 390                 395                 400
Cys Ser Leu Thr Asp Phe Gln Lys Ala Val Tyr Arg Thr Val Leu Glu
                405                 410                 415
Thr Glu Asp Val Thr Leu Ile Leu Gln Ser Ser Glu Pro Cys Thr Cys
                420                 425                 430
Arg Ser Gly Gln Lys Arg Arg Asn Cys Cys Tyr Lys Thr Asn Ser His
        435                 440                 445
Gly Glu Thr Val Lys Thr Leu Tyr Leu Ser Tyr Leu Thr Val Leu Gln
        450                 455                 460
Lys Val Ala Asn His Val Ala Leu Leu Gln Ala Ser Thr Ser Lys
465                 470                 475                 480
Gln Gln Glu Thr Leu Ile Lys Arg Ile Cys Asp Gln Val Phe Ser Arg
                485                 490                 495
Phe Pro Asp Phe Val Gln Lys Ser Lys Asp Ala Ala Phe Glu Thr Leu
                500                 505                 510
Ser Asp Pro Lys Tyr Ser Gly Lys Met Lys Val Leu Gln Gln Leu Leu
                515                 520                 525
```

-continued

```
Asn His Cys Arg Lys Asn Arg Asp Lys Val Leu Leu Phe Ser Phe Ser
    530                 535                 540
Thr Lys Leu Leu Asp Val Leu Gln Gln Tyr Cys Met Ala Ser Gly Leu
545                 550                 555                 560
Asp Tyr Arg Arg Leu Asp Gly Ser Thr Lys Ser Glu Glu Arg Leu Lys
                565                 570                 575
Ile Val Lys Glu Phe Asn Ser Thr Gln Asp Val Asn Ile Cys Leu Val
                580                 585                 590
Ser Thr Met Ala Gly Gly Leu Gly Leu Asn Phe Val Gly Ala Asn Val
            595                 600                 605
Val Val Leu Phe Asp Pro Thr Trp Asn Pro Ala Asn Asp Leu Gln Ala
            610                 615                 620
Ile Asp Arg Ala Tyr Arg Ile Gly Gln Cys Arg Asp Val Lys Val Leu
625                 630                 635                 640
Arg Leu Ile Ser Leu Gly Thr Val Glu Glu Ile Met Tyr Leu Arg Gln
                645                 650                 655
Ile Tyr Lys Gln Gln Leu His Cys Val Val Gly Ser Glu Asn Ala
                660                 665                 670
Lys Arg Tyr Phe Glu Ala Val Gln Gly Ser Lys Glu His Gln Gly Glu
            675                 680                 685
Leu Phe Gly Ile His Asn Leu Phe Lys Phe Arg Ser Gln Gly Ser Cys
            690                 695                 700
Leu Thr Lys Asp Ile Leu Glu Arg Glu Gly Gln Val Glu Ala Gly Ile
705                 710                 715                 720
Met Thr Ala Thr Thr Trp Leu Lys Glu Gly Pro Pro Ala His Lys Leu
                725                 730                 735
Glu Met Pro Arg Gln Pro Asp Cys Gln Glu Cys Arg Gly Thr Glu Gln
                740                 745                 750
Ala Ala Glu Pro Leu Ala Lys Glu Ala Cys Asp Leu Cys Ser Asp Phe
            755                 760                 765
Ser Asp Glu Glu Pro Val Gly Ala Thr Gly Ile Lys Thr Ala Lys Asn
770                 775                 780
Lys Ala Pro Asp Ser Ser Lys Ala Ser Ser Ser Pro Gly Gln Leu Thr
785                 790                 795                 800
Leu Leu Gln Cys Gly Phe Ser Lys Leu Leu Glu Thr Lys Cys Lys Ala
                805                 810                 815
Val Glu Asp Ser Asp Gly Asn Thr Ala Ser Asp Glu Ser Ser Asp
            820                 825                 830
Glu Gln Pro Thr Cys Leu Ser Thr Glu Ala Lys Asp Ala Gly Cys Glu
            835                 840                 845
Lys Asn Gln Asp Ser Leu Gly Thr Ser Lys His Gln Lys Leu Asp Asn
850                 855                 860
Ile Leu Asn Pro Lys Glu Lys His Ile Phe Tyr Lys Ser Glu Lys Ile
865                 870                 875                 880
Leu Glu Gln Asn Ile Ser Ser Lys Ser Asp Glu Lys Ile Lys Asn
                885                 890                 895
Thr Asp Lys His Cys Ile Leu Gln Asn Val Thr Glu Ser Glu Asp Ser
                900                 905                 910
Asp Val Ile Cys Pro Thr Gln Tyr Thr Thr Glu Arg Phe Pro Asp Asn
            915                 920                 925
Ser Leu Arg Phe Lys Pro Pro Leu Glu Gly Ser Glu Asp Ser Glu Thr
930                 935                 940
Glu His Thr Val Lys Thr Arg Asn Asn Asp Asn Ser Arg Asn Thr Asp
```

```
                945                 950                 955                 960

Asp Lys Arg Asn Gly Ile Ile Ser Lys Lys Leu Ser Pro Glu Asn Thr
                965                 970                 975

Thr Leu Lys Ser Ile Leu Lys Arg Lys Gly Thr Ser Asp Ile Ser Asp
                980                 985                 990

Glu Ser Asp Asp Ile Glu Ile Ser Ser Lys Ser Arg Val Arg Lys Arg
                995                 1000                1005

Ala Ser Ser Leu Arg Phe Lys Arg Ile Lys Glu Thr Lys Lys Glu Leu
                1010                1015                1020

His Asn Ser Pro Lys Thr Met Asn Lys Thr Asn Gln Val Tyr Ala Ala
1025                1030                1035                1040

Asn Glu Asp His Asn Ser Gln Phe Ile Asp Asp Tyr Ser Ser Ser Asp
                1045                1050                1055

Glu Ser Leu Ser Val Ser His Phe Ser Phe Ser Lys Gln Ser His Arg
                1060                1065                1070

Pro Arg Thr Ile Arg Asp Arg Thr Ser Phe Ser Ser Lys Leu Pro Ser
                1075                1080                1085

His Asn Lys Lys Asn Ser Thr Phe Ile Pro Arg Lys Pro Met Lys Cys
1090                1095                1100

Ser Asn Glu Lys Val Val Asn Gln Glu Gln Ser Tyr Glu Ser Met Asp
1105                1110                1115                1120

Lys Phe Leu Asp Gly Val Gln Glu Val Ala Tyr Ile His Ser Asn Gln
                1125                1130                1135

Asn Val Ile Gly Ser Ser Lys Ala Glu Asn His Met Ser Arg Trp Ala
                1140                1145                1150

Ala His Asp Val Phe Glu Leu Lys Gln Phe Ser Gln Leu Pro Ala Asn
                1155                1160                1165

Ile Ala Val Cys Ser Ser Lys Thr Tyr Lys Glu Lys Val Asp Ala Asp
                1170                1175                1180

Thr Leu Pro His Thr Lys Lys Gly Gln Gln Pro Ser Glu Gly Ser Ile
1185                1190                1195                1200

Ser Leu Pro Leu Tyr Ile Ser Asn Pro Val Asn Gln Lys Lys Lys Lys
                1205                1210                1215

Val Tyr His Thr Asn Gln Thr Thr Phe Ile Ile Gly Glu Thr Pro Lys
                1220                1225                1230

Gly Ile Arg Arg Tyr Ile Val Ser Asp Asn Thr Ile Leu Glu Glu
                1235                1240                1245

<210> SEQ ID NO 3
<211> LENGTH: 3593
<212> TYPE: DNA
<213> ORGANISM: Homo sapiens

<400> SEQUENCE: 3
catatggcat ccaggagaaa gatgtcttgc cccttctcca gataatggaa aactttgtga    60
agcaagcata aaatctatca cagtggatga aaatggcaag tcatttgcag tcgtcttata   120
tgcagatttt caagaaagga aaatacctct taaacagctt caagaagtga atttgttaa    180 agattgccct aggaatctta tatttgatga tgaagattta gaaaaacctt atttcccaaa   240
ccgaaaattt ccatcatctt ctgttgcttt taaattatct gacaatggag actctactcc   300
ttataccatc aataggtatt tgagagacta ccaaagagaa ggaacccggt ttctttatgg   360
acactacatc catggaggag ggtgcattct gggtgatgac atgggacttg gaaaaacagt   420
acaggttatt tcatttctgg ctgcagtttt gcataaaaag ggaactcgtg aggatattga   480
```

```
aaataacatg ccagagtttt tactaagaag tatgaaaaag gaaccccttt cttctacagc    540
aaaaaagttt ggaatggtca gctgtcattg tggatgaagc tcatagaatc aagaatccaa    600
aagctagagt aacagaagtt atgaaagctt tgaaatgtaa tgtccgcatt ggcctcactg    660
gaaccatcct tcagaacaac atgaaggaac tgtggtgtgt tatggactgg gctgtgccag    720
gccttttagg gagtgggacc tacttcaaga agcagttttc tgacccagta gaacatggtc    780
agagacacac ggcaacaaag agagaactag ccactggccg aaaggccatg caaagacttg    840
ccaaaaagat gtctggctgg tttctcaggc gcaccaagac tcttatcaag gatcagttgc    900
ctaagaagga agaccggatg gtgtattgtt cttttgacaga tttccagaaa gctgtctatc    960
gaacagtgtt agaaacagag gacgtgactt tgatacttca atcttctgag ccttgtacct   1020
gtaggagtgg ccaaaaaagg agaaattgtt gttataagac caattctcat ggtgaaacag   1080
tgaaaacctt gtatctcagt taccttacag tccttcagaa ggtagctaac catgtcgcgc   1140
tactgcaagc tgctagtact tccaaacaac aggaaacact tatcaaaagg atatgtgatc   1200
aggtattttc cagattccca gattttgtgc agaaaagcaa agatgcagcc tttgaaacac   1260
tttctgaccc taaatacagt ggaaaaatga aggtccttca gcagctttta aatcattgca   1320
ggaaaaacag agataaagtt cttctctttt cttttttccac caagttgctt gacgtgctac   1380
agcagtactg tatggcgtct gggcttgatt accgacgact tgatggaagt acaaaatcag   1440
aggaaagact caagattgta aaagagttca cagtacaca agatgttaac atttgccttg   1500
tctctacaat ggctggtgga ctaggcctca attttgtcgg tgccaatgtt gttgtattat   1560
ttgatcctac ttggaatcca gccaatgatc ttcaagccat tgacagagca tataggattg   1620
gacaatgtag agatgtcaaa gtgcttaggc tgatatcctt gggaactgtg gaggaaatca   1680
tgtatttacg acagatatac aagcagcaac ttcactgtgt ggtggttgga agtgaaaatg   1740
ccaaacgata ttttgaagca gttcaaggat ctaaagagca tcaaggagag cttttttgga   1800
tccataacct cttcaaatttt aggtcccaag ggtcttgtct tacgaaggac atcctggaga   1860
gagaaggcca agtagaagca gggatcatga cagccacaac atggttgaaa gagggacctc   1920
cagcacacaa actggaaatg cctagacagc ctgactgtca ggaatgcaga ggtacagaac   1980
aagctgcaga gccactggca aaggaagcat gtgatctctg cagtgacttc agtgatgaag   2040
agccagtggg agccacagga ataaagactg ccaaaaacaa agcacccgat tcaagtaaag   2100
cttccagctc tccaggacag cttaccttac tccagtgtgg tttctcgaaa ttgcttgaaa   2160
caaaatgtaa agcagttgag gatagtgatg gaaatactgc ctctgatgat gaaagttctg   2220
atgagcagcc cacatgcctt tcaacagaag ccaaagatgc tggttgtgag aaaaatcagg   2280
actctcttgg tacttcaaaa catcagaaat tagataacat cctaaatcca aagaaaaagc   2340
atatttttta taaagtgag aagatttttag aacagaatat ttcttccaag tctgacgaga   2400
aaaaaattaa aaatacagat aaacattgca ttttacagaa tgtcacagaa tcagaagata   2460
gtgatgtcat ctgtcctaca caatacacaa ctgagagatt ccccgacaat agtctaaggt   2520
ttaagccacc cttggaagga tctgaggatt ctgaaacaga acacactgta aaacaagaa   2580 ataatgataa tagtcgaaac actgatgaca aagaaatgg aataatttca aaaagttaa   2640 gtcctgagaa cacaaccctg aaatctattt tgaaaagaaa aggcaccagt gatatcagtg   2700
atgaatctga tgcattgaa atttcttcca gtcaagagt aagaaagaga gctagttcat   2760
tgaggtttaa gagaataaaa gaaaccaaaa aagaacttca caattctccc aaaacaatga   2820
```

-continued

```
acaaaacaaa ccaagtgtat gcagcaaatg aggatcataa ctctcagttt attgatgatt    2880
attcatcctc agatgagagt ttatccgtca gccacttcag tttctctaaa cagagccaca    2940
gaccaagaac tataagagac agaactagtt tttcttcaaa attgcctagc cataataaga    3000
aaaatagcac ttttattcca agaaaaccaa tgaaatgttc aaatgagaaa gttgttaatc    3060
aagagcagtc gtatgaatca atggataaat ttttagatgg cgttcaggaa gtggcttata    3120
ttcactcaaa ccagaatgta attggatcga gcaaagctga aaatcacatg agccgatggg    3180
cagcacatga cgtatttgag ttgaagcagt tttctcagct gcctgctaac atagctgttt    3240
gcagttctaa gacatataaa gaaaaagtgg atgcagatac attgccacac acaaagaaag    3300
gccagcaacc gagtgaaggc agcatttcac ttcctctttta catttcaaat cctgtaaacc    3360
agaagaagaa aaaagtctac catacaaacc agaccacctt cataattgga gaaacaccaa    3420
aaggaatccg caggtatatt gtctctgaca atactatact tgaagaataa ttctcaaagg    3480
aaatgtagct cattagtaaa atatgtaaat acttgaatta taaccataac tgacatctga    3540
atatttcaga aaaatctgaa tttcaaaaat aaactgcaaa tgttttagat gct            3593
```

<210> SEQ ID NO 4
<211> LENGTH: 949
<212> TYPE: PRT
<213> ORGANISM: Homo sapiens

<400> SEQUENCE: 4

```
Met Lys Ala Leu Lys Cys Asn Val Arg Ile Gly Leu Thr Gly Thr Ile
  1               5                  10                  15

Leu Gln Asn Asn Met Lys Glu Leu Trp Cys Val Met Asp Trp Ala Val
             20                  25                  30

Pro Gly Leu Leu Gly Ser Gly Thr Tyr Phe Lys Lys Gln Phe Ser Asp
         35                  40                  45

Pro Val Glu His Gly Gln Arg His Thr Ala Thr Lys Arg Glu Leu Ala
     50                  55                  60

Thr Gly Arg Lys Ala Met Gln Arg Leu Ala Lys Lys Met Ser Gly Trp
 65                  70                  75                  80

Phe Leu Arg Arg Thr Lys Thr Leu Ile Lys Asp Gln Leu Pro Lys Lys
                 85                  90                  95

Glu Asp Arg Met Val Tyr Cys Ser Leu Thr Asp Phe Gln Lys Ala Val
            100                 105                 110

Tyr Arg Thr Val Leu Glu Thr Glu Asp Val Thr Leu Ile Leu Gln Ser
        115                 120                 125

Ser Glu Pro Cys Thr Cys Arg Ser Gly Gln Lys Arg Arg Asn Cys Cys
    130                 135                 140

Tyr Lys Thr Asn Ser His Gly Glu Thr Val Lys Thr Leu Tyr Leu Ser
145                 150                 155                 160

Tyr Leu Thr Val Leu Gln Lys Val Ala Asn His Val Ala Leu Leu Gln
                165                 170                 175

Ala Ala Ser Thr Ser Lys Gln Gln Glu Thr Leu Ile Lys Arg Ile Cys
            180                 185                 190

Asp Gln Val Phe Ser Arg Phe Pro Asp Phe Val Gln Lys Ser Lys Asp
        195                 200                 205

Ala Ala Phe Glu Thr Leu Ser Asp Pro Lys Tyr Ser Gly Lys Met Lys
    210                 215                 220

Val Leu Gln Gln Leu Leu Asn His Cys Arg Lys Asn Arg Asp Lys Val
225                 230                 235                 240
```

-continued

```
Leu Leu Phe Ser Phe Ser Thr Lys Leu Leu Asp Val Leu Gln Gln Tyr
            245                 250                 255

Cys Met Ala Ser Gly Leu Asp Tyr Arg Arg Leu Asp Gly Ser Thr Lys
            260                 265                 270

Ser Glu Glu Arg Leu Lys Ile Val Lys Glu Phe Asn Ser Thr Gln Asp
            275                 280                 285

Val Asn Ile Cys Leu Val Ser Thr Met Ala Gly Leu Gly Leu Asn
            290                 295                 300

Phe Val Gly Ala Asn Val Val Leu Phe Asp Pro Thr Trp Asn Pro
305                 310                 315                 320

Ala Asn Asp Leu Gln Ala Ile Asp Arg Ala Tyr Arg Ile Gly Gln Cys
            325                 330                 335

Arg Asp Val Lys Val Leu Arg Leu Ile Ser Leu Gly Thr Val Glu Glu
            340                 345                 350

Ile Met Tyr Leu Arg Gln Ile Tyr Lys Gln Gln Leu His Cys Val Val
            355                 360                 365

Val Gly Ser Glu Asn Ala Lys Arg Tyr Phe Glu Ala Val Gln Gly Ser
            370                 375                 380

Lys Glu His Gln Gly Glu Leu Phe Gly Ile His Asn Leu Phe Lys Phe
385                 390                 395                 400

Arg Ser Gln Gly Ser Cys Leu Thr Lys Asp Ile Leu Glu Arg Glu Gly
            405                 410                 415

Gln Val Glu Ala Gly Ile Met Thr Ala Thr Trp Leu Lys Glu Gly
            420                 425                 430

Pro Pro Ala His Lys Leu Glu Met Pro Arg Gln Pro Asp Cys Gln Glu
            435                 440                 445

Cys Arg Gly Thr Glu Gln Ala Ala Glu Pro Leu Ala Lys Glu Ala Cys
            450                 455                 460

Asp Leu Cys Ser Asp Phe Ser Asp Glu Glu Pro Val Gly Ala Thr Gly
465                 470                 475                 480

Ile Lys Thr Ala Lys Asn Lys Ala Pro Asp Ser Ser Lys Ala Ser Ser
            485                 490                 495

Ser Pro Gly Gln Leu Thr Leu Gln Cys Gly Phe Ser Lys Leu Leu
            500                 505                 510

Glu Thr Lys Cys Lys Ala Val Glu Asp Ser Asp Gly Asn Thr Ala Ser
            515                 520                 525

Asp Asp Glu Ser Ser Asp Glu Gln Pro Thr Cys Leu Ser Thr Glu Ala
            530                 535                 540

Lys Asp Ala Gly Cys Glu Lys Asn Gln Asp Ser Leu Gly Thr Ser Lys
545                 550                 555                 560

His Gln Lys Leu Asp Asn Ile Leu Asn Pro Lys Glu Lys His Ile Phe
            565                 570                 575

Tyr Lys Ser Glu Lys Ile Leu Gln Asn Ile Ser Ser Lys Ser Asp
            580                 585                 590

Glu Lys Lys Ile Lys Asn Thr Asp Lys His Cys Ile Leu Gln Asn Val
            595                 600                 605

Thr Glu Ser Glu Asp Ser Asp Val Ile Cys Pro Thr Gln Tyr Thr Thr
            610                 615                 620

Glu Arg Phe Pro Asp Asn Ser Leu Arg Phe Lys Pro Pro Leu Glu Gly
625                 630                 635                 640

Ser Glu Asp Ser Glu Thr Glu His Thr Val Lys Thr Arg Asn Asn Asp
            645                 650                 655

Asn Ser Arg Asn Thr Asp Asp Lys Arg Asn Gly Ile Ile Ser Lys Lys
```

-continued

```
                          660                 665                 670
    Leu Ser Pro Glu Asn Thr Thr Leu Lys Ser Ile Leu Lys Arg Lys Gly
                675                 680                 685

Thr Ser Asp Ile Ser Asp Glu Ser Asp Ile Glu Ile Ser Ser Lys
        690                 695                 700

Ser Arg Val Arg Lys Arg Ala Ser Ser Leu Arg Phe Lys Arg Ile Lys
    705                 710                 715                 720

Glu Thr Lys Lys Glu Leu His Asn Ser Pro Lys Thr Met Asn Lys Thr
                    725                 730                 735

Asn Gln Val Tyr Ala Ala Asn Glu Asp His Asn Ser Gln Phe Ile Asp
                740                 745                 750

Asp Tyr Ser Ser Asp Glu Ser Leu Ser Val Ser His Phe Ser Phe
                755                 760                 765

Ser Lys Gln Ser His Arg Pro Arg Thr Ile Arg Asp Arg Thr Ser Phe
        770                 775                 780

Ser Ser Lys Leu Pro Ser His Asn Lys Lys Asn Ser Thr Phe Ile Pro
    785                 790                 795                 800

Arg Lys Pro Met Lys Cys Ser Asn Glu Lys Val Val Asn Gln Glu Gln
                    805                 810                 815

Ser Tyr Glu Ser Met Asp Lys Phe Leu Asp Gly Val Gln Glu Val Ala
                820                 825                 830

Tyr Ile His Ser Asn Gln Asn Val Ile Gly Ser Ser Lys Ala Glu Asn
                835                 840                 845

His Met Ser Arg Trp Ala Ala His Asp Val Phe Glu Leu Lys Gln Phe
        850                 855                 860

Ser Gln Leu Pro Ala Asn Ile Ala Val Cys Ser Ser Lys Thr Tyr Lys
    865                 870                 875                 880

Glu Lys Val Asp Ala Asp Thr Leu Pro His Thr Lys Lys Gly Gln Gln
                    885                 890                 895

Pro Ser Glu Gly Ser Ile Ser Leu Pro Leu Tyr Ile Ser Asn Pro Val
                900                 905                 910

Asn Gln Lys Lys Lys Val Tyr His Thr Asn Gln Thr Thr Phe Ile
                915                 920                 925

Ile Gly Glu Thr Pro Lys Gly Ile Arg Arg Tyr Ile Val Ser Asp Asn
        930                 935                 940

Thr Ile Leu Glu Glu
    945

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  synthetic

<400> SEQUENCE: 5

Arg Thr Val Leu Gly Val Ile Gly Asp
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:  synthetic

<400> SEQUENCE: 6
```

```
Arg Thr Ala Leu Gly Asp Ile Gly Asn
  1               5
```

<210> SEQ ID NO 7
<211> LENGTH: 27
<212> TYPE: PRT
<213> ORGANISM: Rat

<400> SEQUENCE: 7

```
Tyr Met Thr Val Ser Ile Ile Asp Arg Phe Met Gln Asp Ser Cys Val
  1               5                  10                  15

Pro Lys Lys Met Leu Gln Leu Val Gly Val Thr
             20                  25
```

<210> SEQ ID NO 8
<211> LENGTH: 28
<212> TYPE: PRT
<213> ORGANISM: Rat

<400> SEQUENCE: 8

```
Lys Phe Arg Leu Leu Gln Glu Thr Met Tyr Met Thr Val Ser Ile Ile
  1               5                  10                  15

Asp Arg Phe Met Gln Asn Ser Cys Val Pro Lys Lys
             20                  25
```

<210> SEQ ID NO 9
<211> LENGTH: 27
<212> TYPE: PRT
<213> ORGANISM: Rat

<400> SEQUENCE: 9

```
Arg Ala Ile Leu Ile Asp Trp Leu Ile Gln Val Gln Met Lys Phe Arg
  1               5                  10                  15

Leu Leu Gln Glu Thr Met Tyr Met Thr Val Ser
             20                  25
```

<210> SEQ ID NO 10
<211> LENGTH: 26
<212> TYPE: PRT
<213> ORGANISM: Rat

<400> SEQUENCE: 10

```
Asp Arg Phe Leu Gln Ala Gln Leu Val Cys Arg Lys Lys Leu Gln Trp
  1               5                  10                  15

Gly Ile Thr Ala Leu Leu Leu Ala Ser Lys
             20                  25
```

<210> SEQ ID NO 11
<211> LENGTH: 18
<212> TYPE: PRT
<213> ORGANISM: Rat

<400> SEQUENCE: 11

```
Met Ser Val Leu Arg Gly Lys Leu Gln Leu Val Gly Thr Ala Ala Met
  1               5                  10                  15

Leu Leu
```

PCNA-ASSOCIATED CELL CYCLE PROTEINS, COMPOSITIONS AND METHODS OF USE

FIELD OF THE INVENTION

The present invention is directed to compositions involved in cell cycle regulation and methods of use. More particularly, the present invention is directed to genes encoding proteins and proteins involved in cell cycle regulation. Methods of use include use in assays screening for modulators of the cell cycle and use as therapeutics.

BACKGROUND OF THE INVENTION

Cells cycle through various stages of growth, starting with the M phase, where mitosis and cytoplasmic division (cytokinesis) occurs. The M phase is followed by the G1 phase, in which the cells resume a high rate of biosynthesis and growth. The S phase begins with DNA synthesis, and ends when the DNA content of the nucleus has doubled. The cell then enters G2 phase, which ends when mitosis starts, signaled by the appearance of condensed chromosomes. Terminally differentiated cells are arrested in the G1 phase, and no longer undergo cell division.

The hallmark of a malignant cell is uncontrolled proliferation. This phenotype is acquired through the accumulation of gene mutations, the majority of which promote passage through the cell cycle. Cancer cells ignore growth regulatory signals and remain committed to cell division. Classic oncogenes, such as ras, lead to inappropriate transition from G1 to S phase of the cell cycle, mimicking proliferative extracellular signals. Cell cycle checkpoint controls ensure faithful replication and segregation of the genome. The loss of cell cycle checkpoint control results in genomic instability, greatly accelerating the accumulation of mutations which drive malignant transformation. Thus, modulating cell cycle checkpoint pathways and other such pathways with therapeutic agents could exploit the differences between normal and tumor cells, both improving the selectivity of radio- and chemotherapy, and leading to novel cancer treatments. As another example, it would be useful to control entry into apoptosis.

On the other hand, it is also sometimes desirable to enhance proliferation of cells in a controlled manner. For example, proliferation of cells is useful in wound healing and where growth of tissue is desirable. Thus, identifying modulators which promote, enhance or deter the inhibition of proliferation is desirable.

Despite the desirability of identifying cell cycle components and modulators, there is a deficit in the field of such compounds. Accordingly, it would be advantageous to provide compositions and methods useful in screening for modulators of the cell cycle. It would also be advantageous to provide novel compositions which are involved in the cell cycle.

SUMMARY OF THE INVENTION

The present invention provides cell cycle proteins and nucleic acids which encode such proteins. Also provided are methods for screening for a bioactive agent capable of modulating the cell cycle. The method comprises combining a cell cycle protein and a candidate bioactive agent and a cell or a population of cells, and determining the effect on the cell in the presence and absence of the candidate agent. Therapeutics for regulating or modulating the cell cycle are also provided.

In one aspect, a recombinant nucleic acid encoding a cell cycle protein of the present invention comprises a nucleic acid that hybridizes under high stringency conditions to a sequence complementary to that set forth in FIG. 1 (SEQ ID NO: 1) or FIG. 3 (SEQ ID NO: 3). In a preferred embodiment, the cell cycle protein provided herein binds to proliferation cell nuclear antigen (PCNA).

In one embodiment, a recombinant nucleic acid is provided which comprises a nucleic acid sequence as set forth in FIG. 1 (SEQ ID NO: 1) or FIG. 3 (SEQ ID NO: 3). In another embodiment, a recombinant nucleic acid encoding a cell cycle protein is provided which comprises a nucleic acid sequence having at least 85% sequence identity to a sequence as set forth in FIG. 1 (SEQ ID NO: 1) or FIG. 3 (SEQ ID NO: 3). In a further embodiment, provided herein is a recombinant nucleic acid encoding an amino acid sequence as depicted in FIG. 2 (SEQ ID NO: 2) or FIG. 4 (SEQ ID NO: 4).

In another aspect of the invention, expression vectors are provided. The expression vectors comprise one or more of the recombinant nucleic acids provided herein operably linked to regulatory sequences recognized by a host cell transformed with the nucleic acid. Further provided herein are host cells comprising the vectors and recombinant nucleic acids provided herein. Moreover, provided herein are processes for producing a cell cycle protein comprising culturing a host cell as described herein under conditions suitable for expression of the cell cycle protein. In one embodiment, the process includes recovering the cell cycle protein.

Also provided herein are recombinant cell cycle proteins encoded by the nucleic acids of the present invention. In one aspect, a recombinant polypeptide is provided herein which comprises an amino acid sequence having at least 80% sequence identity with a sequence as set forth in FIG. 2 (SEQ ID NO: 2) or FIG. 4 (SEQ ID NO: 4). In one embodiment, a recombinant cell cycle protein is provided which comprises an amino acid sequence as set forth in FIG. 2 (SEQ ID NO: 2) or FIG. 4 (SEQ ID NO: 4).

In another aspect, the present invention provides isolated polypeptides which specifically bind to a cell cycle protein as described herein. Examples of such isolated polypeptides include antibodies. Such an antibody can be a monoclonal antibody. In one embodiment, such an antibody reduces or eliminates the biological function of said cell cycle protein.

Further provided herein are methods for screening for a bioactive agent capable of binding to a cell cycle protein. In one embodiment the method comprises combining a cell cycle protein and a candidate bioactive agent, and determining the binding of said candidate bioactive agent to said cell cycle protein.

In another aspect, provided herein is a method for screening for a bioactive agent capable of interfering with the binding of a cell cycle protein and a PCNA protein. In one embodiment, such a method comprises combining a cell cycle protein, a candidate bioactive agent and a PCNA protein, and determining the binding of the cell cycle protein and the PCNA protein. If desired, the cell cycle protein and the PCNA protein can be combined first.

Further provided herein are methods for screening for a bioactive agent capable of modulating the activity of cell cycle protein. In one embodiment the method comprises adding a candidate bioactive agent to a cell comprising a recombinant nucleic acid encoding a cell cycle protein, and determining the effect of the candidate bioactive agent on the cell. In a preferred embodiment, a library of candidate bioactive agents is added to a plurality of cells comprising a recombinant nucleic acid encoding a cell cycle protein.

Other aspects of the invention will become apparent to the skilled artisan by the following description of the invention.

BRIEF DESCRIPTION OF THE DRAWINGS

FIGS. 1A–1B (SEQ ID NO: 1) depict a nucleotide sequence of cell cycle protein Radh—isoform 1. A translation start codon (ATG), an in frame upstream termination codon (TGA) and translation termination codon (TAA) are in bold and underlined.

FIG. 2 (SEQ ID NO: 2) depicts an amino acid sequence of cell cycle protein Radh—isoform 1. Putative bipartite nuclear localization signals are at positions 351–368, 374–391, 962–979 and 999–1016. A putative tudor domain found in proteins associated with nucleoprotein complexes is at positions 21–81. A putative DNA/RNA helicase domain (DEAD/DEAH box) is at positions 517–635.

FIGS. 3A–3B (SEQ ID NO: 3) depict a nucleotide sequence of cell cycle protein Radh—isoform 2. A translation start codon (ATG), an in frame upstream termination codon (TGA) and translation termination codon (TAA) are in bold and underlined.

FIG. 4 (SEQ ID NO: 4) depicts an amino acid sequence of cell cycle protein Radh—isoform 2.

DETAILED DESCRIPTION OF THE INVENTION

The present invention provides cell cycle proteins and nucleic acids which encode such proteins. Also provided are methods for screening for a bioactive agent capable of modulating the cell cycle. In one aspect, the method comprises combining a cell cycle protein and a candidate bioactive agent and a cell or a population of cells, and determining the effect on the cell(s) in the presence and absence of the candidate agent. Other screening assays including binding assays are also provided herein as described below. Therapeutics for regulating or modulating the cell cycle are also provided and described herein. Diagnostics, as further described below, are also provided herein.

A cell cycle protein of the present invention may be identified in several ways. "Protein" in this sense includes proteins, polypeptides, and peptides. The cell cycle proteins of the invention fall into two general classes: proteins that are completely novel, i.e. are not part of a public database as of the time of discovery, although they may have homology to either known proteins or peptides encoded by expressed sequence tags (ESTs). Alternatively, the cell cycle proteins are known proteins, but that were not known to be involved in the cell cycle; i.e. they are identified herein as having a novel biological function. Accordingly, a cell cycle protein may be initially identified by its association with a protein known to be involved in the cell cycle. Wherein the cell cycle proteins and nucleic acids are novel, compositions and methods of use are provided herein. In the case that the cell cycle proteins and nucleic acids were known but not known to be involved in cell cycle activity as described herein, methods of use, i.e. functional screens, are provided.

In one embodiment provided herein, a cell cycle protein, as defined herein, has one or more of the following characteristics: binding to PCNA; homology to yeast RAD26 and human ERCC6; and cell cycle protein activity as described herein. PCNA, yeast RAD26 and human ERCC6 are further discussed below. In one aspect, the homology to yeast RAD26 and human ERCC6 is found using e.g., the BLAST search program in GenBank [Altschul et al., Nucl. Acids Res. 25:3389–3402 (1997)]. More particularly, in one embodiment, the following parameters were used to determine sequences having homology to isoform 1 herein. Database: non-redundant GenBank CDS translations+PDB+SwissProt+SPupdate+PIR; Lambda of 0.316; K of 0.132; and H of 0.00; Gapped Lambda of 0.27; K of 0.047 and H of 4.94e-324; the Matrix is BLOSUM62; Gap Penalties: existence: 11, extension: 1. Similarly, in one embodiment, the following parameters were used for the homology search of isoform 2 herein. Database: non-redundant GenBank CDS translations+PDB+SwissProt+SPupdate+PIR; Lambda of 0.315; K of 0.131; and H of 0.00; Gapped Lambda of 0.27; K of 0.047 and H of 4.94e-324; the Matrix is BLOSUM62; Gap Penalties: existence: 11, extension: 1.

In one embodiment, the cell cycle protein is termed Radh. The characteristics described below can apply to any of the cell cycle proteins provided herein, however, Radh is used for illustrative purposes. Radh has similarity to proteins belonging to a family of helicases. DNA helicases remove the supercoiling of DNA, or unwind DNA so that replication can occur. Preferably, Radh binds to PCNA. PCNA interacts with proteins including those involved in cell cycle progression, checkpoint control, DNA replication and repair [Fotedar and Fotedar, Prog. Cell Cycle Res. 1:73–89 (1995); Prosperi, Prog. Cell Cycle Res. 3:193–210 (1997); Kelman and Hurwitz, Trends Biochem. Sci. 23(7):236–8 (1998)]. Observations point to the p53 tumor suppressor protein as a regulator of PCNA expression, which seems to be compatible with the function of p53 as an inducer of DNA repair, and PCNA, as a DNA repair protein [Morris et al., Proc. Natl. Acad. Sci. U.S.A. 93(2):895–9 (1996)]. Moreover, PCNA has been implicated in mismatch repair [Kolodner and Marsischky, Curr. Opin. Genet. Dev. 9(1):89–96 (1999)]. Regarding PCNA, also see, e.g., Warbrick, Bioessays 20(3):195–9 (1998).

ERCC6, to which Radh shares some homology, contains seven consecutive domains conserved between DNA and RNA helicases. The novel cell cycle proteins provided herein share greater homology with the sequences in the figures than do ERCC6, yeast RAD26, or other known proteins. A study reports that analysis of ERCC6 indicates that it is (i) involved in Cockayne's syndrome, (ii) it is specific for preferential repair of transcribed genes, and (iii) it is not essential for cell viability [Troelstra et al., Cell 71 (6):939–53 (1992)]. Cells from patients with the UV-sensitive nucleotide excision repair disorder Cockayne's syndrome (CS) have a specific defect in transcription-coupled repair. Two genes defective in Cockayne syndrome, CSA and CSB, have been identified and ERCC6 was shown to correct the defect of CS complementation group B [CSB; Troelstra, supra]. Regarding ERCC6, also see Selby and Sancar, J. Biol. Chem. 272(3):1885–90 (1997) and Huang, et al., Biochem Biophys Res Commun, 201(1):310–7 (1994).

Yeast protein RAD26, to which Radh also shares some homology, has been identified as the functional yeast homolog of the Cockayne syndrome B gene ERCC6 [van Gool et al., EMBO J., 13(22)5361–9 (1994); Tijsterman and Brouwer, J. Biol. Chem. 274(3):1199–202 (1999)]. RAD26 is involved with transcription-coupled DNA repair which is responsible for removal of damaged DNA from transcribed strands of RNA polymerase 11 transcribed sequences. Studies suggest that RAD26 mutant cells engage in transcription but then thwart the process by withholding the release of the transcription complex at the damaged sites (Tijsterman and Brouwer, supra).

In preferred embodiments, the Radh proteins of the invention belong to a set of proteins involved in the error-prone repair mechanism, especially for UV-induced DNA damage whereby UV radiation has damaged or removed nucleotides in a base pair so that the repair proteins replace the missing nucleotides randomly. Most preferably, Radh proteins bind to proteins such as PCNA and participate in the activation of a repair cascade—either directly or indirectly.

In one embodiment, cell cycle nucleic acids or cell cycle proteins are initially identified by substantial nucleic acid and/or amino acid sequence identity or similarity to the sequence(s) provided herein. In a preferred embodiment, cell cycle nucleic acids or cell cycle proteins have sequence identity or similarity to the sequences provided herein as described below and one or more of the cell cycle protein bioactivities as further described below. Such sequence identity or similarity can be based upon the overall nucleic acid or amino acid sequence.

In a preferred embodiment, a protein is a "cell cycle protein" as defined herein, if the overall sequence identity of the amino acid sequence to the amino acid sequences in FIG. 2 or 4 is preferably greater than about 75%, more preferably greater than about 80%, even more preferably greater than about 85% and most preferably greater than 90%. In some embodiments the sequence identity will be as high as about 93 to 95 or 98%.

In another preferred embodiment, a cell cycle protein has an overall sequence similarity with the amino acid sequences of FIG. 2 (SEQ ID NO: 2) or 4 (SEQ ID NO: 4) of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, *Nucl. Acid Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology*, 266: 460–480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et aL Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences set forth in FIG. 1 (SEQ ID NO: 1) or 3 (SEQ ID NO: 3), it is understood that in one embodiment, the percentage of sequence identity will be determined based on the number of identical amino acids in relation to the total number of amino acids. Thus, for example, sequence identity of sequences shorter than that shown in FIG. 2 (SEQ ID NO: 2) or 4 (SEQ ID NO: 4), as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein. Cell cycle proteins of the present invention may be shorter or longer than the amino acid sequence encoded by the nucleic acid shown in FIG. 1 (SEQ ID NO: 1) or 3 (SEQ ID NO: 3). Thus, in a preferred embodiment, included within the definition of cell cycle proteins are portions or fragments of the amino acid sequence encoded by the nucleic acid sequence provided herein. In one embodiment herein, fragments of cell cycle proteins are considered cell cycle proteins if a) they share at least one antigenic epitope; b) have at least the indicated sequence identity; c) and preferably have cell cycle biological activity as further defined herein. In some cases, where the sequence is used diagnostically, that is, when the presence or absence of cell cycle protein nucleic acid is determined, only the indicated sequence identity is required. The nucleic acids of the present invention may also be shorter or longer than the sequence in FIG. 1 (SEQ ID NO: 1) or 3 (SEQ ID NO: 3). The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, cell cycle proteins can be made that are longer than those depicted in FIG. 2 (SEQ ID NO: 2) or 4 (SEQ ID NO: 4); for example, by the addition of epitope or purification tags, the addition of other fusion sequences, or the elucidation of additional coding and non-coding sequences. As described below, the fusion of a cell cycle peptide to a fluorescent peptide, such as Green Fluorescent Peptide (GFP), is particularly preferred.

Cell cycle proteins may also be identified as encoded by cell cycle nucleic acids which hybridize to the sequence depicted in FIG. 1 (SEQ ID NO: 1) or 3 (SEQ ID NO: 3), or the complement thereof, as outlined herein. Hybridization conditions are further described below.

In a preferred embodiment, when a cell cycle protein is to be used to generate antibodies, a cell cycle protein must share at least one epitope or determinant with the full length protein. By "epitope" or "determinant" herein is meant a portion of a protein which will generate and/or bind an antibody. Thus, in most instances, antibodies made to a smaller cell cycle protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibodies to a cell cycle protein are capable of reducing or eliminating the biological function of the cell cycle proteins described herein, as is described below.

That is, the addition of anti-cell cycle protein antibodies (either polyclonal or preferably monoclonal) to cell cycle proteins (or cells containing cell cycle proteins) may reduce or eliminate the cell cycle protein activity. Generally, at least a 25% decrease in activity is preferred, with at least about 50% being particularly preferred and about a 95–100% decrease being especially preferred.

The cell cycle antibodies of the invention specifically bind to cell cycle proteins. In a preferred embodiment, the antibodies specifically bind to cell cycle proteins. By "specifically bind" herein is meant that the antibodies bind to the protein with a binding constant in the range of at least $10^{-4}$–$10^{-6}$M$^{-1}$, with a preferred range being $10^{-7}$–$10^{-9}$M$^{-1}$. Antibodies are further described below.

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to the nucleic acid sequence of FIG. 1 or 3 is preferably greater than 75%, more preferably greater than about 80%, particularly greater than about 85% and most preferably greater than 90%. In some embodiments the sequence identity will be as high as about 93 to 95 or 98%.

In a preferred embodiment, a cell cycle nucleic acid encodes a cell cycle protein. As will be appreciated by those in the art, due to the degeneracy of the genetic code, an extremely large number of nucleic acids may be made, all of which encode the cell cycle proteins of the present invention. Thus, having identified a particular amino acid sequence, those skilled in the art could make any number of different nucleic acids, by simply modifying the sequence of one or more codons in a way which does not change the amino acid sequence of the cell cycle protein.

In one embodiment, the nucleic acid is determined through hybridization studies. Thus, for example, nucleic acids which hybridize under high stringency to the nucleic acid sequence shown in the Figure, or its complement is considered a cell cycle nucleic acid. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 300° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The cell cycle proteins and nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the Figures also include the complement of the sequence. By the term "recombinant nucleic acid" herein is meant nucleic acid, originally formed in vitro, in general, by the manipulation of nucleic acid by endonucleases, in a form not normally found in nature. Thus an isolated cell cycle nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a cell cycle protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides cell cycle protein variants. These variants fall into one or more of three classes: substitutional, insertional or deletional variants. These variants ordinarily are prepared by site specific mutagenesis of nucleotides in the DNA encoding a cell cycle protein, using cassette or PCR mutagenesis or other techniques well known in the art, to produce DNA encoding the variant, and thereafter expressing the DNA in recombinant cell culture as outlined above. However, variant cell cycle protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the cell cycle protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cell cycle variants screened for the optimal combination of desired activity. Techniques for making substitution mutations at predetermined sites in DNA having a known sequence are well known, for example, M13 primer mutagenesis and PCR mutagenesis. Screening of the mutants is done using assays of cell cycle protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cell cycle protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the cell cycle proteins as needed. Alternatively, the variant may be designed such that the biological activity of the cell cycle protein is altered. For example, glycosylation sites may be altered or removed.

Covalent modifications of cell cycle polypeptides are included within the scope of this invention. One type of covalent modification includes reacting targeted amino acid residues of a cell cycle polypeptide with an organic derivatizing agent that is capable of reacting with selected side chains or the N-or C-terminal residues of a cell cycle polypeptide. Derivatization with bifunctional agents is useful, for instance, for crosslinking cell cycle proteins to a water-insoluble support matrix or surface for use in the method for purifying anti-cell cycle antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the cell cycle polypeptide included within the scope of this invention comprises altering the native glycosylation pattern of the polypeptide. "Altering the native glycosylation pattern" is intended for purposes herein to mean deleting one or more carbohydrate moieties found in native sequence cell cycle polypeptide, and/or adding one or more glycosylation sites that are not present in the native sequence cell cycle polypeptide.

Addition of glycosylation sites to cell cycle polypeptides may be accomplished by altering the amino acid sequence thereof. The alteration may be made, for example, by the addition of, or substitution by, one or more serine or threonine residues to the native sequence cell cycle polypeptide (for O-linked glycosylation sites). The cell cycle amino acid sequence may optionally be altered through changes at the DNA level, particularly by mutating the DNA encoding the cell cycle polypeptide at preselected bases such that codons are generated that will translate into the desired amino acids.

Another means of increasing the number of carbohydrate moieties on the cell cycle polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the cell cycle polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.* 138:350 (1987).

Another type of covalent modification of cell cycle proteins comprises linking the cell cycle polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Cell cycle polypeptides of the present invention may also be modified in a way to form chimeric molecules comprising a cell cycle polypeptide fused to another, heterologous polypeptide or amino acid sequence. In one embodiment, such a chimeric molecule comprises a fusion of a cell cycle polypeptide with a tag polypeptide which provides an epitope to which an anti-tag antibody can selectively bind. The epitope tag is generally placed at the amino-or carboxyl-terminus of the cell cycle polypeptide. The presence of such epitope-tagged forms of a cell cycle polypeptide can be detected using an antibody against the tag polypeptide. Also, provision of the epitope tag enables the cell cycle polypeptide to be readily purified by affinity purification using an anti-tag antibody or another type of affinity matrix that binds to the epitope tag. In an alternative embodiment, the chimeric molecule may comprise a fusion of a cell cycle polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecula and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an embodiment herein, cell cycle proteins of the cell cycle family and cell cycle proteins from other organisms are cloned and expressed as outlined below. Thus, probe or degenerate polymerase chain reaction (PCR) primer sequences may be used to find other related cell cycle proteins from humans or other organisms. As will be appreciated by those in the art, particularly useful probe and/or PCR primer sequences include the unique areas of the cell cycle nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant cell cycle nucleic acid can be further-used as a probe to identify and isolate other cell cycle nucleic acids. It can also be used as a "precursor" nucleic acid to make modified or variant cell cycle nucleic acids and proteins.

Using the nucleic acids of the present invention which encode a cell cycle protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cell cycle protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the cell cycle protein; for example, transcriptional and translational regulatory nucleic acid sequences from Bacillus are preferably used to express the cell cycle protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Cell cycle proteins of the present invention are produced by culturing a host cell transformed with an expression vector containing nucleic acid encoding a cell cycle protein, under the appropriate conditions to induce or cause expression of the cell cycle protein. The conditions appropriate for cell cycle protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are Drosophila meangaster cells, Saccharomyces cerevisiae and other yeasts, E. coli, Bacillus subtilis, SF9 cells, C129 cells, 293 cells, Neurospora, BHK, CHO, COS, and HeLa cells, fibroblasts, Schwanoma cell lines, immortalized mammalian myeloid and lymphoid cell lines, and tumor cell lines.

In a preferred embodiment, the cell cycle proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for cell cycle protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase 11 to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, cell cycle proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cell cycle protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cell cycle protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, cell cycle proteins are produced in insect cells. Expression vectors for the transformation of insect cells, and in particular, baculovirus-based expression vectors, are well known in the art.

In a preferred embodiment, cell cycle proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The cell cycle protein may also be made as a fusion protein, using techniques well known in the art. Thus, for example, for the creation of monoclonal antibodies, if the desired epitope is small, the cell cycle protein may be fused to a carrier protein to form an immunogen. Alternatively, the cell cycle protein may be made as a fusion protein to increase expression, or for other reasons. For example, when the cell cycle protein is a cell cycle peptide, the nucleic acid encoding the peptide may be linked to other nucleic acid for expression purposes. Similarly, cell cycle proteins of the invention can be linked to protein labels, such as green fluorescent protein (GFP), red fluorescent protein (RFP), blue fluorescent protein (BFP), yellow fluorescent protein (YFP), etc.

In one embodiment, the cell cycle nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the cell cycle protein is purified or isolated after expression. Cell cycle proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cell cycle protein may be purified using a standard anti-cell cycle antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the cell cycle protein. In some instances no purification will be necessary.

Once expressed and purified if necessary, the cell cycle proteins and nucleic acids are useful in a number of applications.

The nucleotide sequences (or their complement) encoding cell cycle proteins have various applications in the art of molecular biology, including uses as hybridization probes, in chromosome and gene mapping and in the generation of anti-sense RNA and DNA. A cell cycle protein encoding nucleic acid will also be useful for the preparation of cell cycle polypeptides by the recombinant techniques described herein.

The full-length native sequence cell cycle protein gene, or portions thereof, may be used as hybridization probes for a cDNA library to isolate other genes (for instance, those encoding naturally-occurring variants of cell cycle protein or cell cycle protein from other species) which have a desired sequence identity to the cell cycle protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the cell cycle protein gene using the known DNA sequence to synthesize a selected probe of about 40 bases. Hybridization probes may be labeled by a variety of labels, including radionucleotides such as $^{32}p$ or $^{35}S$, or enzymatic labels such as alkaline phosphatase coupled to the probe via avidin/biotin coupling systems. Labeled probes having a sequence complementary to that of the cell cycle protein gene of the present invention can be used to screen libraries of human cDNA, genomic DNA or mRNA to determine which members of such libraries the probe hybridizes.

Nucleotide sequences encoding a cell cycle protein can also be used to construct hybridization probes for mapping the gene which encodes that cell cycle protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

A nucleic acid which encodes a cell cycle protein or its modified form can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a cell cycle protein can be used to clone genomic DNA encoding a cell cycle protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the cell cycle protein transgene incorporation with tissue-specific enhancers. Transgenic animals that include a copy of a transgene encoding a cell cycle protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the cell cycle protein can be used to construct a cell cycle protein "knock out" animal which has a defective or altered gene encoding a cell cycle protein as a result of homologous recombination between the endogenous gene encoding a cell cycle protein and altered genomic DNA encoding a cell cycle protein introduced into an embryonic cell of the animal. For example, cDNA encoding a cell cycle protein can be used to clone genomic DNA encoding a cell cycle protein in accordance with established techniques. A portion of the genomic DNA encoding a cell cycle protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the cell cycle polypeptide.

It is understood that the models described herein can be varied. For example, "knock-in" models can be formed, or the models can be cell-based rather than animal models.

Nucleic acid encoding the cell cycle polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et a., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

In a preferred embodiment, the cell cycle proteins, nucleic acids, variants, modified proteins, cells and/or transgenics containing the said nucleic acids or proteins are used in screening assays. Identification of the cell cycle protein provided herein permits the design of drug screening assays for compounds that bind or interfere with the binding to the cell cycle protein and for compounds which modulate cell cycle activity.

Preferred embodiments utilize the human cell cycle protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative cell cycle proteins may be used, including cell cycle proteins having at least one amino acid substitution, deletion or insertion as outlined above.

In a preferred embodiment, the methods comprise combining a cell cycle protein and a candidate bioactive agent, and determining the binding of the candidate agent to the cell cycle protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to alter cell cycling, may be used. For example, p21 is a molecule known to arrest cells in the G1 cell phase, by binding G1 cyclin-CDK complexes.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a pro babilistically sufficient range of diversity to allow binding to a particular target.

Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), 0-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Enql., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Left., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In one embodiment of the methods described herein, portions of cell cycle proteins are utilized; in a preferred embodiment, portions having cell cycle activity are used. Cell cycle protein activity is described further below and includes binding activity to PCNA or cell cycle protein modulators as further described below. In addition, the assays described herein may utilize either isolated cell cycle proteins or cells comprising the cell cycle proteins.

Generally, in a preferred embodiment of the methods herein, for example for binding assays, the cell cycle protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In some embodiments, PCNA can be used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the cell cycle protein is bound to the support, and a candidate bioactive agent is added to the assay. Alternatively, the candidate agent is bound to the support and the cell cycle protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the cell cycle protein may be done in a number of ways. In a preferred embodiment, the candidate bioactive agent is labelled, and binding determined directly. For example, this may be done by attaching all or a portion of the cell cycle protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e., cell cycle protein), such as an antibody, peptide, binding partner, ligand, etc. In a preferred embodiment, the competitor is PCNA. Under certain circumstances, there may be competitive binding as between the bioactive agent and the binding moiety, with the binding moiety displacing the bioactive agent. This assay can be used to determine candidate agents which interfere with binding between cell cycle proteins and PCNA. "Interference of binding" as used herein means that native binding of the cell cycle protein differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the cell cycle protein and thus is capable of binding to, and potentially modulating, the activity of the cell cycle protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the cell cycle protein with a higher affinity. Thus, if the candidate bioactive agent is labeled, the presence of the label on the support, coupled with a lack of competitor binding, may indicate that the candidate agent is capable of binding to the cell cycle protein.

In a preferred embodiment, the methods comprise differential screening to identity bioactive agents that are capable of modulating the activity of the cell cycle proteins. Such assays can be done with the cell cycle protein or cells comprising said cell cycle protein. In one embodiment, the methods comprise combining a cell cycle protein and a competitor in a first sample. A second sample comprises a candidate bioactive agent, a cell cycle protein and a competitor. The binding of the competitor is determined for both samples, and a change, or difference in binding between the two samples indicates the presence of an agent capable of binding to the cell cycle protein and potentially modulating its activity. That is, if the binding of the competitor is different in the second sample relative to the first sample, the agent is capable of binding to the cell cycle protein.

Alternatively, a preferred embodiment utilizes differential screening to identify drug candidates that bind to the native cell cycle protein, but cannot bind to modified cell cycle proteins. The structure of the cell cycle protein may be modeled, and used in rational drug design to synthesize agents that interact with that site. Drug candidates that affect cell cycle protein bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of cell cycle may also be done. In a preferred embodiment, methods for screening for a bioactive agent capable of modulating the activity of cell cycle comprise the steps of adding a candidate bioactive agent to a sample of a cell cycle protein (or cells comprising a cell cycle protein) and determining an alteration in the biological activity of the cell cycle protein. "Modulating the activity of a cell cycle protein" includes an increase in activity, a decrease in activity, or a change in the type or kind of activity present. Thus, in this embodiment, the candidate agent should both bind to the cell cycle protein(although this may not be necessary), and alter its biological or biochemical activity as defined herein. The methods include both in vitro screening methods, as are generally outlined above, and in vivo screening of cells for alterations in the presence, distribution, activity or amount of cell cycle protein.

Thus, in this embodiment, the methods comprise combining a cell cycle sample and a candidate bioactive agent, and evaluating the effect on the cell cycle. By "cell cycle protein activity" or grammatical equivalents herein is meant one or more of the cell cycle protein's biological activities, including, but not limited to, ability to affect the cell cycle, bind to PCNA, compete with other proteins for binding to PCNA, modulate DNA replication, modulate defects associated with Cockayne Syndrome B, modulate unwinding of nucleic acid molecules, modulate PCNA and modulate mismatch repair.

In a preferred embodiment, the activity of the cell cycle protein is decreased; in another preferred embodiment, the activity of the cell cycle protein is increased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a cell cycle protein. The methods comprise adding a candidate bioactive agent, as defined above, to a cell comprising cell cycle proteins. Preferred cell types include almost any cell. The cells contain a recombinant nucleic acid that encodes a cell cycle protein. In a preferred embodiment, a library of candidate agents are tested on a plurality of cells.

Detection of cell cycle regulation may be done as will be appreciated by those in the art. In one embodiment, indicators of the cell cycle are used. There are a number of parameters that may be evaluated or assayed to allow the detection of alterations in cell cycle regulation, including, but not limited to, cell viability assays, assays to determine whether cells are arrested at a particular cell cycle stage ("cell proliferation assays"), and assays to determine at which cell stage the cells have arrested ("cell phase assays"). By assaying or measuring one or more of these parameters, it is possible to detect not only alterations in cell cycle regulation, but alterations of different steps of the cell cycle regulation pathway. This may be done to evaluate native cells, for example to quantify the aggressiveness of a tumor cell type, or to evaluate the effect of candidate drug agents that are being tested for their effect on cell cycle regulation. In this manner, rapid, accurate screening of candidate agents may be performed to identify agents that modulate cell cycle regulation.

Thus, the present compositions and methods are useful to elucidate bioactive agents that can cause a cell or a population of cells to either move out of one growth phase and into another, or arrest in a growth phase. In some embodiments, the cells are arrested in a particular growth phase, and it is desirable to either get them out of that phase or into a new phase. Alternatively, it may be desirable to force a cell to arrest in a phase, for example G1, rather than continue to move through the cell cycle. Similarly, it may be desirable in some circumstances to accelerate a non-arrested but slowly moving population of cells into either the next phase or just through the cell cycle, or to delay the onset of the next phase. For example, it may be possible to alter the activities of certain enzymes, for example kinases, phosphatases, proteases or ubiquitination enzymes, that contribute to initiating cell phase changes.

In a preferred embodiment, the methods outlined herein are done on cells that are not arrested in the G1 phase; that is, they are rapidly or uncontrollably growing and replicating, such as tumor cells. In this manner, candidate agents are evaluated to find agents that can alter the cell cycle regulation, i.e. cause the cells to arrest at cell cycle checkpoints, such as in G1 (although arresting in other phases such as S, G2 or M are also desirable). Alternatively, candidate agents are evaluated to find agents that can cause proliferation of a population of cells, i.e. that allow cells that are generally arrested in G1 to start proliferating again; for example, peripheral blood cells, terminally differentiated cells, stem cells in culture, etc.

Accordingly, the invention provides methods for screening for alterations in cell cycle regulation of a population of cells. By "alteration" or "modulation" (used herein interchangeably), is generally meant one of two things. In a preferred embodiment, the alteration results in a change in the cell cycle of a cell, i.e. a proliferating cell arrests in any one of the phases, or an arrested cell moves out of its arrested phase and starts the cell cycle, as compared to another cell or in the same cell under different conditions. Alternatively, the progress of a cell through any particular phase may be altered; that is, there may be an acceleration or delay in the length of time it takes for the cells to move thorough a particular growth phase. For example, the cell may be normally undergo a G1 phase of several hours; the addition of an agent may prolong the G1 phase.

The measurements can be determined wherein all of the conditions are the same for each measurement, or under various conditions, with or without bioactive agents, or at different stages of the cell cycle process. For example, a measurement of cell cycle regulation can be determined in a cell or cell population wherein a candidate bioactive agent is present and wherein the candidate bioactive agent is absent. In another example, the measurements of cell cycle regulation are determined wherein the condition or environment of the cell or populations of cells differ from one another. For example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the measurements of cell cycle regulation are determined at different stages of the cell cycle process. In yet another example, the measurements of cell cycle regulation are taken wherein the conditions are the same, and the alterations are between one cell or cell population and another cell or cell population.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

In a preferred embodiment, the methods comprise assaying one or more of several different cell parameters, including, but not limited to, cell viability, cell proliferation, and cell phase. Other parameters include participation in DNA replication, mismatch repair, coupling with CSB, and unwinding of nucleic acid molecules.

In a preferred embodiment, cell viability is assayed, to ensure that a lack of cellular change is due to experimental conditions (i.e. the introduction of a candidate bioactive agent) not cell death. There are a variety of suitable cell viability assays which can be used, including, but not limited to, light scattering, viability dye staining, and exclusion dye staining.

In a preferred embodiment, a light scattering assay is used as the viability assay, as is well known in the art. For example, when viewed in the FACS, cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90° scatter; similarly, membrane blebbing can alter the forward scatter. Alterations in the intensity of light scattering, or the cell-refractive index indicate alterations in viability.

Thus, in general, for light scattering assays, a live cell population of a particular cell type is evaluated to determine it's forward and side scattering properties. This sets a standard for scattering that can subsequently be used.

In a preferred embodiment, the viability assay utilizes a viability dye. There are a number of known viability dyes that stain dead or dying cells, but do not stain growing cells. For example, annexin V is a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Suitable viability dyes include, but are not limited to, annexin, ethidium homodimer-1, DEAD Red, propidium iodide, SYTOX Green, etc., and others known in the art; see the Molecular Probes Handbook of Fluorescent Probes and Research Chemicals, Haugland, Sixth Edition, hereby incorporated by reference; see Apoptosis Assay on page 285 in particular, and Chapter 16.

Protocols for viability dye staining for cell viability are known, see Molecular Probes catalog, supra. In this embodiment, the viability dye such as annexin is labeled, either directly or indirectly, and combined with a cell population. Annexin is commercially available, i.e., from PharMingen, San Diego, Calif., or Caltag Laboratories, Millbrae, Calif. Preferably, the viability dye is provided in a solution wherein the dye is in a concentration of about 100 ng/ml to about 500 ng/ml, more preferably, about 500 ng/ml to about 1 µg/ml, and most preferably, from about 1 µg/ml to about 5 µg/ml. In a preferred embodiment, the viability dye is directly labeled; for example, annexin may be labeled with a fluorochrome such as fluorecein isothiocyanate (FITC), Alexa dyes, TRITC, AMCA, APC, tri-color, Cy-5, and others known in the art or commercially available. In an alternate preferred embodiment, the viability dye is labeled with a first label, such as a hapten such as biotin, and a secondary fluorescent label is used, such as fluorescent streptavidin. Other first and second labeling pairs can be used as will be appreciated by those in the art.

Once added, the viability dye is allowed to incubate with the cells for a period of time, and washed, if necessary. The cells are then sorted as outlined below to remove the non-viable cells.

In a preferred embodiment, exclusion dye staining is used as the viability assay. Exclusion dyes are those which are excluded from living cells, i.e. they are not taken up passively (they do not permeate the cell membrane of a live cell). However, due to the permeability of dead or dying cells, they are taken up by dead cells. Generally, but not always, the exclusion dyes bind to DNA, for example via intercalation. Preferably, the exclusion dye does not fluoresce, or fluoresces poorly, in the absence of DNA; this eliminates the need for a wash step. Alternatively, exclusion dyes that require the use of a secondary label may also be used. Preferred exclusion dyes include, but are not limited to, ethidium bromide; ethidium homodimer-1; propidium iodine; SYTOX green nucleic acid stain; Calcein AM, BCECF AM; fluorescein diacetate; TOTO® and TO-PRO™

(from Molecular Probes; supra, see chapter 16) and others known in the art.

Protocols for exclusion dye staining for cell viability are known, see the Molecular Probes catalog, supra. In general, the exclusion dye is added to the cells at a concentration of from about 100 ng/ml to about 500 ng/ml, more preferably, about 500 ng/ml to about 1 µg/ml, and most preferably, from about 0.1 µg/ml to about 5 µg/ml, with about 0.5 µg/ml being particularly preferred. The cells and the exclusion dye are incubated for some period of time, washed, if necessary, and then the cells sorted as outlined below, to remove non-viable cells from the population.

In addition, there are other cell viability assays which may be run, including for example enzymatic assays, which can measure extracellular enzymatic activity of either live cells (i.e. secreted proteases, etc.), or dead cells (i.e. the presence of intracellular enzymes in the media; for example, intracellular proteases, mitochondrial enzymes, etc.). See the Molecular Probes Handbook of Fluorescent Probes and Research Chemicals, Haugland, Sixth Edition, hereby incorporated by reference; see chapter 16 in particular.

In a preferred embodiment, at least one cell viability assay is run, with at least two different cell viability assays being preferred, when the fluors are compatible. When only 1 viability assay is run, a preferred embodiment utilizes light scattering assays (both forward and side scattering). When two viability assays are run, preferred embodiments utilize light scattering and dye exclusion, with light scattering and viability dye staining also possible, and all three being done in some cases as well. Viability assays thus allow the separation of viable cells from non-viable or dying cells.

In addition to a cell viability assay, a preferred embodiment utilizes a cell proliferation assay. By "proliferation assay" herein is meant an assay that allows the determination that a cell population is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook, supra; chapter 15 in particular.

In general, inclusion dyes are provided to the cells at a concentration ranging from about 100 ng/ml to about 5 µg/ml, with from about 500 ng/ml to about 1 µg/ml being preferred. A wash step may or may not be used. In a preferred embodiment, a candidate bioactive agent is combined with the cells as described herein. The cells and the inclusion dye are incubated for some period of time, to allow cell division and thus dye dilution. The length of time will depend on the cell cycle time for the particular cells; in general, at least about 2 cell divisions are preferred, with at least about 3 being particularly preferred and at least about 4 being especially preferred. The cells are then sorted as outlined below, to create populations of cells that are replicating and those that are not. As will be appreciated by those in the art, in some cases, for example when screening for anti-proliferation agents, the bright (i.e. fluorescent) cells are collected; in other embodiments, for example for screening for proliferation agents, the low fluorescence cells are collected. Alterations are determined by measuring the fluorescence at either different time points or in different cell populations, and comparing the determinations to one another or to standards.

In a preferred embodiment, the proliferation assay is an antimetabolite assay. In general, antimetabolite assays find the most use when agents that cause cellular arrest in G1 or G2 resting phase is desired. In an antimetabolite proliferation assay, the use of a toxic antimetabolite that will kill dividing cells will result in survival of only those cells that are not dividing. Suitable antimetabolites include, but are not limited to, standard chemotherapeutic agents such as methotrexate, cisplatin, taxol, hydroxyurea, nucleotide analogs such as AraC, etc. In addition, antimetabolite assays may include the use of genes that cause cell death upon expression.

The concentration at which the antimetabolite is added will depend on the toxicity of the particular antimetabolite, and will be determined as is known in the art. The antimetabolite is added and the cells are generally incubated for some period of time; again, the exact period of time will depend on the characteristics and identity of the antimetabolite as well as the cell cycle time of the particular cell population. Generally, a time sufficient for at least one cell division to occur.

In a preferred embodiment, at least one proliferation assay is run, with more than one being preferred. Thus, a proliferation assay results in a population of proliferating cells and a population of arrested cells. In one embodiment, other known proliferation assays may be used, i.e., those known in the art such as a colorimetric assay.

In a preferred embodiment, either after or simultaneously with one or more of the proliferation assays outlined above, at least one cell phase assay is done. A "cell phase" assay determines at which cell phase the cells are arrested, M, G1, S, or G2.

In a preferred embodiment, the cell phase assay is a DNA binding dye assay. Briefly, a DNA binding dye is introduced to the cells, and taken up passively. Once inside the cell, the DNA binding dye binds to DNA, generally by intercalation, although in some cases, the dyes can be either major or minor groove binding compounds. The amount of dye is thus directly correlated to the amount of DNA in the cell, which varies by cell phase; G2 and M phase cells have twice the DNA content of G1 phase cells, and S phase cells have an intermediate amount, depending on at what point in S phase the cells are. Suitable DNA binding dyes are permeant, and include, but are not limited to, Hoechst 33342 and 33258, acridine orange, 7-AAD, LDS 751, DAPI, and SYTO 16, Molecular Probes Handbook, supra; chapters 8 and 16 in particular.

In general, the DNA binding dyes are added in concentrations ranging from about 1 μg/ml to about 5 μg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating and thus contain more than a single genome of DNA. Alterations are determined by measuring the fluorescence at either different time points or in different cell populations, and comparing the determinations to one another or to standards.

In a preferred embodiment, the cell phase assay is a cyclin destruction assay. In this embodiment, prior to screening (and generally prior to the introduction of a candidate bioactive agent, as outlined below), a fusion nucleic acid is introduced to the cells. The fusion nucleic acid comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each with a different fluor, such that detection of the cell phase can occur.

A number of cyclin destruction boxes are known in the art, for example, cyclin A has a destruction box comprising the sequence RTVLGVIGD (SEQ ID NO: 5; the destruction box of cyclin B1 comprises the sequence RTALGDIGN (SEQ ID NO: 6). See Glotzer et al., Nature 349:132–138 (1991). Other destruction boxes are known as well: YMTVSIIDRFMQDSCVPKKMLQLVGVT (SEQ ID NO: 7) (rat cyclin B); KFRLLQETMYMTVSIIDRFMQN-SCVPKK (SEQ ID NO: 8) (mouse cyclin B); RAILID-WLIQVQMKFRLLQETMYMTVS (SEQ ID NO: 9) (mouse cyclin B1); DRFLQAQLVCRKKLQVVGI-TALLLASK (SEQ ID NO: 10) (mouse cyclin B2); and MSVLRGKLQLVGTAAMLL (SEQ ID NO: 11) (mouse cyclin A2).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a detectable molecule. By "detectable molecule" herein is meant a molecule that allows a cell or compound comprising the detectable molecule to be distinguished from one that does not contain it, i.e., an epitope, sometimes called an antigen TAG, a specific enzyme, or a fluorescent molecule. Preferred fluorescent molecules include but are not limited to green fluorescent protein (GFP), blue fluorescent protein (BFP), yellow fluorescent protein (YFP), red fluorescent protein (RFP), and enzymes including luciferase and β-galactosidase. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred. Similarly, enzymatic detectable molecules may also be used; for example, an enzyme that generates a novel or chromogenic product.

Accordingly, the results of sorting after cell phase assays generally result in at least two populations of cells that are in different cell phases.

The proteins and nucleic acids provided herein can also be used for screening purposes wherein the protein-protein interactions of the cell cycle proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463, a preferred system is described in Serial Nos. 09/050,863, filed Mar. 30, 1998, and 09/359,081, filed Jul. 22, 1999, both entitled "Mammalian Protein Interaction Cloning System". For use in conjunction with these systems, a particularly useful shuttle vector is described in Serial No. 09/133,944, filed Aug. 14, 1998, entitled "Shuttle Vectors".

In general, two nucleic acids are transformed into a cell, where one is a "bait" such as the gene encoding a cell cycle protein or a portion thereof, and the other encodes a test candidate. Only if the two expression products bind to one another will an indicator, such as a fluorescent protein, be expressed. Expression of the indicator indicates when a test candidate binds to the cell cycle protein and can be identified as an cell cycle protein. Using the same system and the identified cell cycle proteins the reverse can be performed. Namely, the cell cycle proteins provided herein can be used to identify new baits, or agents which interact with cell cycle proteins. Additionally, the two-hybrid system can be used wherein a test candidate is added in addition to the bait and the cell cycle protein encoding nucleic acids to determine agents which interfere with the bait, such as PCNA, and the cell cycle protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for cell cycle activity are described above. The activity assays, such as having an effect on the cell cycle, binding to PCNA, DNA replication, Cockayne Syndrome B, supercoiling and modulate mismatch repair can be performed to confirm the activity of cell cycle proteins which have already been identified by their sequence identity/similarity or binding to PCNA, as well as to further confirm the activity of lead compounds identified as modulators of cell cycle protein activity.

The components provided herein for the assays provided herein may also be combined to form kits. The kits can be based on the use of the protein and/or the nucleic acid encoding the cell cycle proteins. In one embodiment, other components are provided in the kit. Such components include one or more of packaging, instructions, antibodies, and labels. Additional assays such as those used in diagnostics are further described below.

In this way, bioactive agents are identified. Compounds with pharmacological activity are able to enhance or interfere with the activity of the cell cycle protein. The compounds having the desired pharmacological activity may be administered in a physiologically acceptable carrier to a host, as further described below.

The present discovery relating to the role of cell cycle proteins in the cell cycle thus provides methods for inducing or preventing cell proliferation in cells. In a preferred embodiment, the cell cycle proteins, and particularly cell cycle protein fragments, are useful in the study or treatment of conditions which are mediated by the cell cycle proteins, i.e. to diagnose, treat or prevent cell cycle associated disorders. Thus, "cell cycle associated disorders" or "disease state" include conditions involving both insufficient or excessive cell proliferation. Examples include cancer and Cockayne Syndrome B.

Thus, in one embodiment, cell cycle regulation in cells or organisms is provided. In one embodiment, the methods comprise administering to a cell or individual in need thereof, a cell cycle protein in a therapeutic amount. Alternatively, an anti-cell cycle antibody that reduces or eliminates the biological activity of the endogenous cell cycle protein is administered. In another embodiment, a bioactive agent as identified by the methods provided herein is administered. Alternatively, the methods comprise administering to a cell or individual a recombinant nucleic acid encoding a cell cycle protein. As will be appreciated by those in the art, this may be accomplished in any number of ways. In a preferred embodiment, the activity of cell cycle protein is increased by increasing the amount of cell cycle protein in the cell, for example by overexpressing the endogenous cell cycle protein or by administering a gene encoding a cell cycle protein, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entirety.

Without being bound by theory, it appears that cell cycle protein is an important protein in the cell cycle. Accordingly, disorders based on mutant or variant cell cycle genes may be determined. In one embodiment, the invention provides methods for identifying cells containing variant cell cycle genes comprising determining all or part of the sequence of at least one endogenous cell cycle genes in a cell. As will be appreciated by those in the art, this may be done using any number of sequencing techniques. In a preferred embodiment, the invention provides methods of identifying the cell cycle genotype of an individual comprising determining all or part of the sequence of at least one cell cycle gene of the individual. This is generally done in at least one tissue of the individual, and may include the evaluation of a number of tissues or different samples of the same tissue. The method may include comparing the sequence of the sequenced cell cycle gene to a known cell cycle gene, i.e. a wild-type gene.

The sequence of all or part of the cell cycle gene can then be compared to the sequence of a known cell cycle gene to determine if any differences exist. This can be done using any number of known sequence identity programs, such as Bestfit, etc. In a preferred embodiment, the presence of a difference in the sequence between the cell cycle gene of the patient and the known cell cycle gene is indicative of a disease state or a propensity for a disease state.

In one embodiment, the invention provides methods for diagnosing a cell cycle related condition in an individual. The methods comprise measuring the activity of cell cycle in a tissue from the individual or patient, which may include a measurement of the amount or specific activity of a cell cycle protein. This activity is compared to the activity of cell cycle from either an unaffected second individual or from an unaffected tissue from the first individual. When these activities are different, the first individual may be at risk for a cell cycle associated disorder. In this way, for example, monitoring of various disease conditions may be done, by monitoring the levels of the protein or the expression of mRNA therefor. Similarly, expression levels may correlate to the prognosis.

In one aspect, the expression levels of cell cycle protein genes are determined in different patient samples or cells for which either diagnosis or prognosis information is desired. Gene expression monitoring is done on genes encoding cell cycle proteins. In one aspect, the expression levels of cell cycle protein genes are determined for different cellular states, such as normal cells and cells undergoing apoptosis or transformation. By comparing cell cycle protein gene expression levels in cells in different states, information including both up- and down-regulation of cell cycle protein genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important cell cycle protein genes, such as those of the present invention, which can then be used in these screens. These methods can also be done on the protein basis; that is, protein expression levels of the cell cycle proteins can be evaluated for diagnostic purposes or to screen candidate agents. In addition, the cell cycle protein nucleic acid sequences can be administered for gene therapy purposes, including the administration of antisense nucleic acids, or the cell cycle proteins administered as therapeutic drugs.

Cell cycle protein sequences bound to biochips include both nucleic acid and amino acid sequences as defined above. In a preferred embodiment, nucleic acid probes to cell cycle protein nucleic acids (both the nucleic acid sequences having the sequences outlined in the Figures and/or the complements thereof are made. The nucleic acid probes attached to the biochip are designed to be substantially complementary to the cell cycle protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix Gene-Chip™ technology.

"Differential expression," or grammatical equivalents as used herein, refers to both qualitative as well as quantitative differences in the genes temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology 14:1675–1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the cell cycle protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a cell cycle protein is detected by binding the digoxygenin with an anti-digoxygenin secondary antibody and developed with nitro blue tetrazolium and 5-bromo-4-chloro-3-indoyl phosphate.

In another preferred method, expression of cell cycle proteins is performed using in situ imaging techniques employing antibodies to cell cycle proteins. In this method cells are contacted with from one to many antibodies to the cell cycle proteins. Following washing to remove non-specific antibody binding, the presence of the antibody or antibodies is detected. In one embodiment the antibody is detected by incubating with a secondary antibody that contains a detectable label. In another method the primary antibody to the cell cycle proteins contains a detectable label. In another preferred embodiment each one of multiple primary antibodies contains a distinct and detectable label. This method finds particular use in simultaneous screening for a pluralilty of cell cycle proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblofting (Western blotting), immunoprecipitation, BIACORE technology, and the like.

In one embodiment, the cell cycle proteins of the present invention may be used to generate polyclonal and monoclonal antibodies to cell cycle proteins, which are useful as described herein. Similarly, the cell cycle proteins can be coupled, using standard technology, to affinity chromatography columns. These columns may then be used to purify anti-cell cycle protein antibodies. In a preferred embodiment, the antibodies are generated to epitopes unique to the cell cycle protein; that is, the antibodies show little or no cross-reactivity to other proteins. These antibodies find use in a number of applications. For example, the anti-cell cycle protein antibodies may be coupled to standard affinity chromatography columns and used to purify cell cycle proteins as further described below. The antibodies may also be used as blocking polypeptides, as outlined above, since they will specifically bind to the cell cycle protein.

The anti-cell cycle protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the cell cycle polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-cell cycle protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the cell cycle polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against cell cycle protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-cell cycle protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boemer et al. are also available for the preparation of human monoclonal antibodies (Cole et al., *Monoclonal Antibodies and Cancer Therapy*, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al, Nature 368 856–859 (1994); Morrison, Nature 368, 812–13 (1994); Fishwild etal., Nature Biotechnology 14, 845–51 (1996); Neuberger, Nature Biotechnology 14, 826 (1996); Lonberg and Huszar, Intern. Rev. Immunol. 13 65–93 (1995).

Bispecific antibodies are monoclonal, preferably human or humanized, antibodies that have binding specificities for at least two different antigens. In the present case, one of the binding specificities is for the cell cycle protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-cell cycle protein antibodies of the invention have various utilities. For example, anti-cell cycle protein antibodies may be used in diagnostic assays for a cell cycle protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-cell cycle protein antibodies also are useful for the affinity purification of cell cycle protein from recombinant cell culture or natural sources. In this process, the antibodies against cell cycle protein are immobilized on a suitable support, such a Sephadex resin or filter paper, using methods well known in the art. The immobilized antibody then is contacted with a sample containing the cell cycle protein to be purified, and thereafter the support is washed with a suitable solvent that will remove substantially all the material in the sample except the cell cycle protein, which is bound to the immobilized antibody. Finally, the support is washed with another suitable solvent that will release the cell cycle protein from the antibody.

The anti-cell cycle protein antibodies may also be used in treatment. In one embodiment, the genes encoding the antibodies are provided, such that the antibodies bind to and modulate the cell cycle protein within the cell.

In one embodiment, a therapeutically effective dose of a cell cycle protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for cell cycle protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the cell cycle protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise a cell cycle protein, agonist or antagonist (including antibodies and bioactive agents as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of cell cycle protein related disorders with an antibody raised against cell cycle proteins. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a cell cycle protein antigen to which antibodies are raised. As appreciated by one of ordinary skill in the art, the cell cycle protein antigen may be provided by injecting a cell cycle polypeptide against which antibodies are desired to be raised into a recipient, or contacting the recipient with a cell cycle protein encoding nucleic acid, capable of expressing the cell cycle protein antigen, under conditions for expression of the cell cycle protein antigen.

In a preferred embodiment, a therapeutic compound is conjugated to an antibody, preferably an anti-cell cycle protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer, and cell cycle protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, cell cycle protein genes are administered as DNA vaccines, either single genes or combinations of cell cycle protein genes. Naked DNA vaccines are generally known in the art; see Brower, Nature Biotechnology 16:1304–1305 (1998). Methods for the use of genes as DNA vaccines are well known to one of ordinary skill in the art, and include placing a cell cycle protein gene or portion of a cell cycle protein gene under the control of a promoter for expression in a patient. The cell cycle protein gene used for DNA vaccines can encode full-length cell cycle proteins, but more preferably encodes portions of the cell cycle proteins including peptides derived from the cell cycle protein. In a preferred embodiment a patient is immunized with a DNA vaccine comprising a plurality of nucleotide sequences derived from a cell cycle protein gene. Similarly, it is possible to immunize a patient with a plurality of cell cycle protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing cell cycle proteins.

In a preferred embodiment, the DNA vaccines include a gene encoding an adjuvant molecule with the DNA vaccine. Such adjuvant molecules include cytokines that increase the immunogenic response to the cell cycle polypeptide encoded by the DNA vaccine. Additional or alternative adjuvants are known to those of ordinary skill in the art and find use in the invention.

Other variations in accordance with the invention are apparent to those skilled in the art. All references cited herein are expressly incorporated by reference in their entirety. Moreover all sequences and accession numbers cited or displayed in said references are incorporated herein.

We claim:

1. A recombinant nucleic acid encoding the cell cycle protein RADH, comprising a nucleic acid sequence having at least about 95% identity to the full length nucleic acid sequence set forth in SEQ ID NO:1, wherein said RADH protein will bind to proliferating cell nuclear antigen (PCNA).

2. A recombinant nucleic acid encoding the cell cycle protein RADH, comprising anucleic acid sequence having at least about 95% identity to the full length nucleic acid sequence set forth in SEQ ID NO:3, wherein said RADH protein will bind to PCNA.

3. A recombinant nucleic acid encoding the cell cycle protein RADH, comprising the full length nucleic acid sequence set forth in SEQ ID NO:1, wherein said RADH protein will bind to PCNA.

4. A recombinant nucleic acid encoding the cell cycle protein RADH, comprising the full length nucleic acid sequence set forth in SEQ ID NO:3, wherein said RADH protein will bind to PCNA.

5. A recombinant nucleic acid encoding the cell cycle protein RADH, wherein said RADH protein comprises an amino acid sequence having at least about 95% identity to the full length amino acid sequence set forth in SEQ ID NO:2, wherein said RADH protein will bind to PCNA.

6. A recombinant nucleic acid encoding the cell cycle protein RADH, wherein said RADH protein comprises an amino acid sequence having at least about 95% identity to the full length amino acid sequence set forth in SEQ ID NO:4, wherein said RADH protein will bind to PCNA.

7. A recombinant nucleic acid encoding the cell cycle protein RADH, wherein said RADH protein comprises the full length amino acid sequence set forth in SEQ ID NO:2.

8. A recombinant nucleic acid encoding the cell cycle protein RADH, wherein said RADH protein comprises the full length amino acid sequence set forth in SEQ ID NO:4.

9. An expression vector, comprising a recombinant nucleic acid according to any one of claims 1–8, operably linked to regulatory sequences recognized by a host cell transformed with said recombinant nucleic acid.

10. A host cell, comprising a recombinant nucleic acid according to any one of claims 1–8.

11. A host cell, comprising an expression vector according to claim 9.

12. A process for producing the cell cycle protein RADH, comprising culturing the host cell of claim 11 under conditions suitable for expression of said RADH protein.

13. A process according to claim 12, further comprising recovering said RADH protein.

* * * * *